(12) United States Patent
Qi et al.

(10) Patent No.: US 8,454,557 B1
(45) Date of Patent: Jun. 4, 2013

(54) INFUSION PUMP SYSTEM AND METHOD

(75) Inventors: Wenkang Qi, Cupertino, CA (US);
Tracy Brewer, Hayward, CA (US);
Hans Crommenacker, Cupertino, CA (US)

(73) Assignee: Asante Solutions, Inc., Sunnyvale, CA (US)

( * ) Notice: Subject to any disclaimer, the term of this patent is extended or adjusted under 35 U.S.C. 154(b) by 0 days.

(21) Appl. No.: 13/553,027

(22) Filed: Jul. 19, 2012

(51) Int. Cl.
*A61M 5/172* (2006.01)

(52) U.S. Cl.
USPC .......................................... 604/67; 604/151

(58) Field of Classification Search
USPC ................... 604/67, 131–133, 141, 151–152, 604/154–158
See application file for complete search history.

(56) References Cited

U.S. PATENT DOCUMENTS

| | | | |
|---|---|---|---|
| 4,745,564 A * | 5/1988 | Tennes et al. | 702/141 |
| 4,855,711 A * | 8/1989 | Harrop et al. | 473/467 |
| 6,126,595 A | 10/2000 | Amano et al. | |
| 6,233,471 B1 | 5/2001 | Berner et al. | |
| 6,371,218 B1 * | 4/2002 | Amano et al. | 173/183 |
| 6,461,331 B1 | 10/2002 | Van Antwerp | |
| 6,474,219 B2 | 11/2002 | Klitmose et al. | |
| 6,485,461 B1 | 11/2002 | Mason et al. | |
| 6,508,788 B2 | 1/2003 | Preuthun | |
| 6,524,280 B2 | 2/2003 | Hansen et al. | |
| 6,533,183 B2 | 3/2003 | Aasmul et al. | |
| 6,537,251 B2 | 3/2003 | Klitmose | |
| 6,540,672 B1 | 4/2003 | Simonsen et al. | |
| 6,544,229 B1 | 4/2003 | Danby et al. | |
| 6,547,764 B2 | 4/2003 | Larsen et al. | |
| 6,551,276 B1 | 4/2003 | Mann et al. | |
| 6,554,798 B1 | 4/2003 | Mann et al. | |
| 6,554,800 B1 | 4/2003 | Nezhadian et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,562,011 B1 | 5/2003 | Buch-Rasmussen et al. | |
| 6,564,105 B2 | 5/2003 | Starkweather et al. | |
| 6,569,126 B1 | 5/2003 | Poulsen et al. | |
| 6,571,128 B2 | 5/2003 | Lebel et al. | |
| 6,572,542 B1 | 6/2003 | Houben | |
| 6,577,899 B2 | 6/2003 | Lebel et al. | |
| 6,582,404 B1 | 6/2003 | Klitgaard et al. | |

(Continued)

FOREIGN PATENT DOCUMENTS

| | | |
|---|---|---|
| CA | 2543545 | 5/2005 |
| DE | 196 27 619 A | 1/1998 |

(Continued)

OTHER PUBLICATIONS

Collins and Lee, "Microfluidic flow transducer based on the measurement of electrical admittance," *Lab Chip*, 2003, 12 pages.

(Continued)

*Primary Examiner* — Quynh-Nhu H Vu
(74) *Attorney, Agent, or Firm* — Fish & Richardson P.C.

(57) ABSTRACT

Some embodiments of an infusion pump system may be configured to detect when at least one component of the pump system is exposed to an impact above a threshold level. In particular embodiments, the infusion pump system can be equipped with an impact detection system that can sense when an impact above the threshold level has occurred to the pump device, which thereby enables the infusion pump system to initiate appropriate patient safety countermeasures.

19 Claims, 14 Drawing Sheets

U.S. PATENT DOCUMENTS

| | | |
|---|---|---|
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann et al. |
| 7,029,455 B2 | 4/2006 | Flaherty |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 7,730,764 B2 * | 6/2010 | Tachibana et al. ........... 73/12.06 |
| 2001/0056262 A1 | 12/2001 | Cabiri et al. |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0104982 A1 | 6/2003 | Wittmann et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Estes |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2008/0125700 A1 * | 5/2008 | Moberg et al. ................. 604/67 |
| 2008/0172027 A1 | 7/2008 | Blomquist |
| 2008/0306444 A1 | 12/2008 | Brister et al. |
| 2011/0306927 A1 * | 12/2011 | Watanabe et al. ............... 604/67 |

FOREIGN PATENT DOCUMENTS

| | | |
|---|---|---|
| DE | 102 36 669 | 2/2004 |
| DE | 20 2005 012 358 | 10/2005 |
| EP | 0 496 141 | 7/1992 |
| EP | 0 612 004 | 8/1994 |
| EP | 0 580 723 | 10/1995 |
| EP | 1 045 146 | 10/2000 |

| | | |
|---|---|---|
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/093648 | 11/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/075016 | 7/2006 |
| WO | WO 2006/105792 | 10/2006 |
| WO | WO 2006/105793 | 10/2006 |
| WO | WO 2006/105794 | 10/2006 |

OTHER PUBLICATIONS

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Medtronic News Release, "Medtronic Receives FDA Approval for World's First Insulin Pump with Real-time Continuous Glucose Monitoring," Apr. 13, 2006, 3 pages.

Patent Abstracts of Japan, vol. 1999, No. 04, and JP 11 010036 , Apr. 30, 1999 and Jan. 19, 1999, Toray Ind. Inc.

* cited by examiner

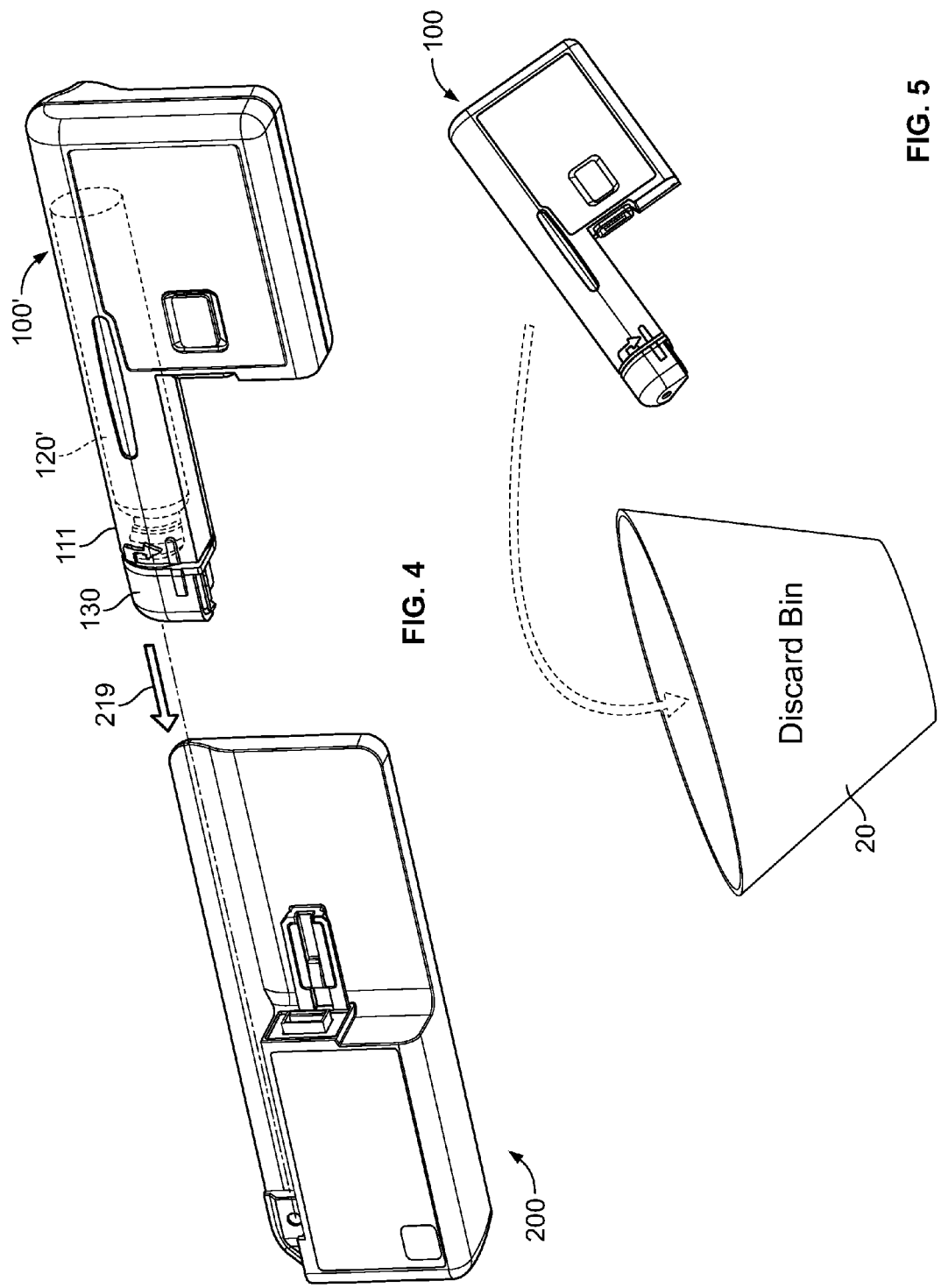

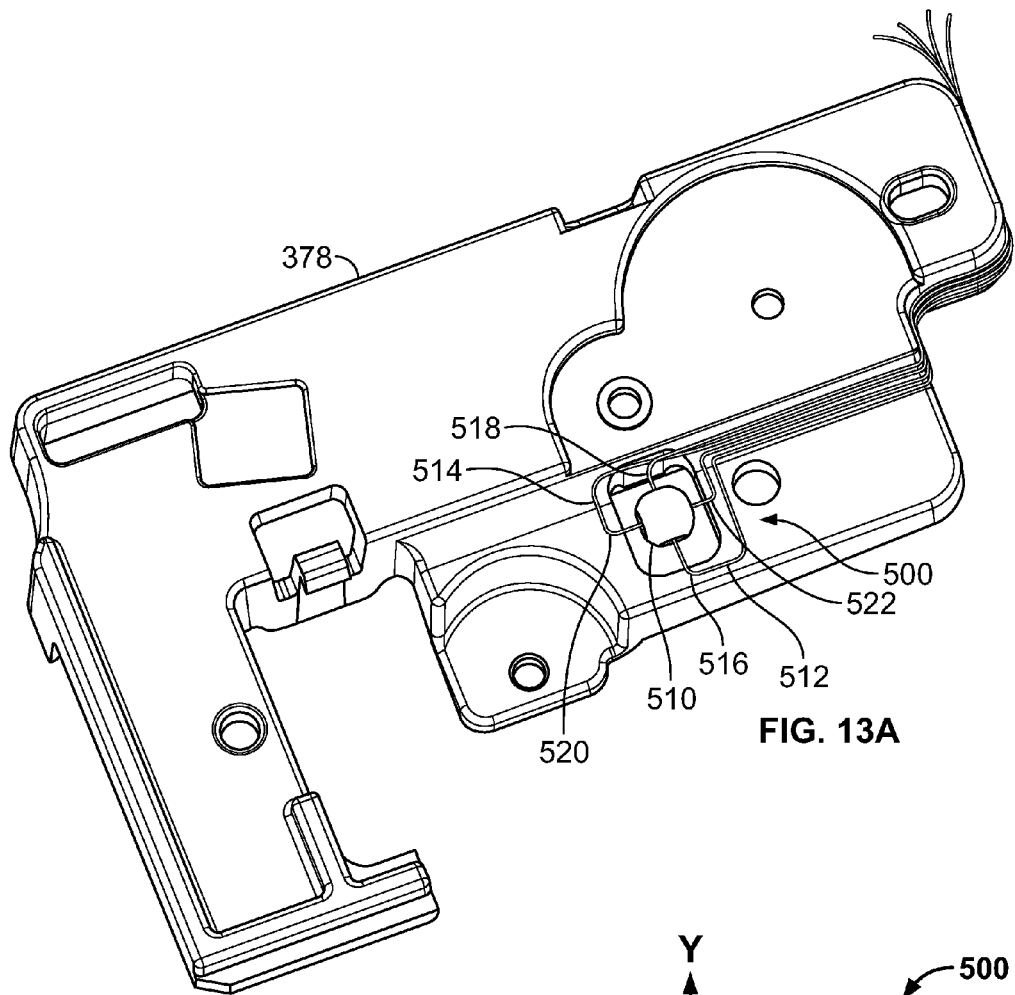
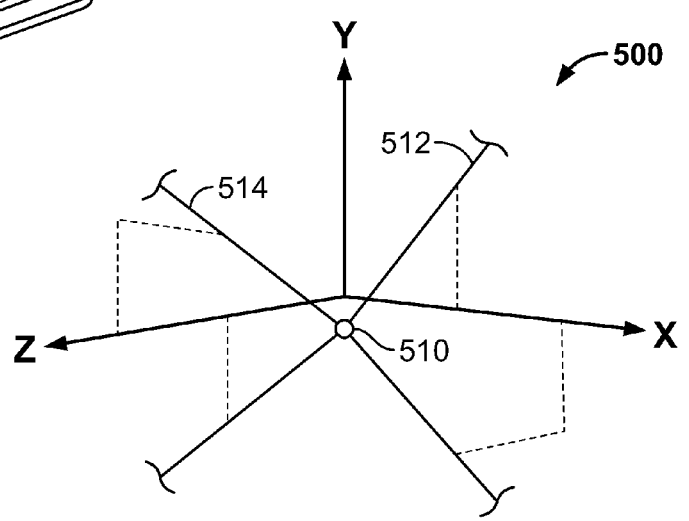
FIG. 13A
FIG. 13B

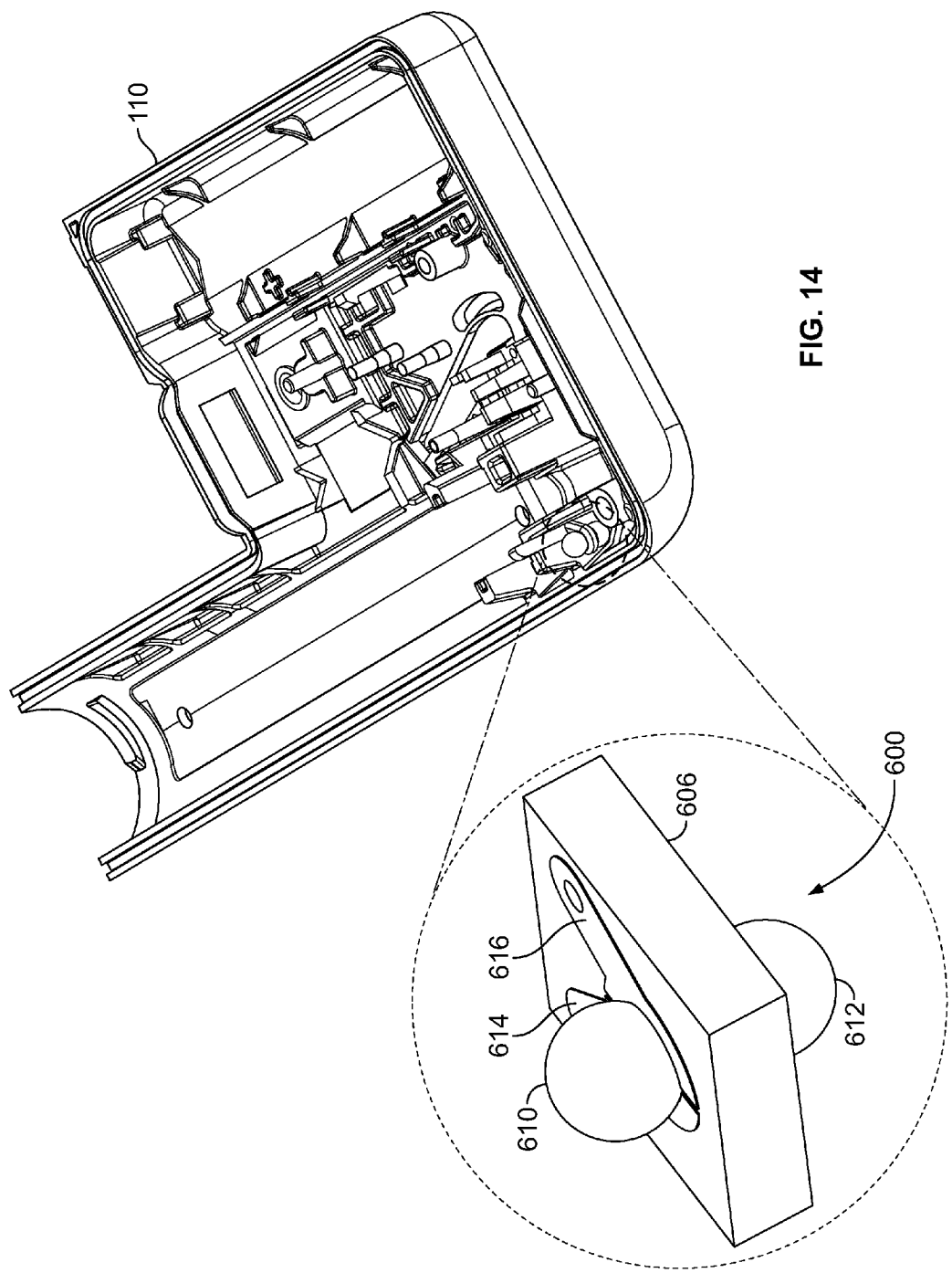

INFUSION PUMP SYSTEM AND METHOD

TECHNICAL FIELD

This document relates to an infusion pump system, such as a portable infusion pump system for dispensing a medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Infusion pump devices often need to deliver medicine in accurately controlled dosages. Over-dosages and under-dosages of medicine can be detrimental to patients. For example, an infusion pump device that delivers an over-dosage or under-dosage of insulin to a diabetes patient can significantly affect the blood-glucose level of the patient.

In some circumstances, the ability of an infusion pump to deliver an accurately controlled dosage can be negatively affected if the pump device has sustained damage from a physical impact. Damage to an infusion pump device may result, for example, from dropping the infusion pump device onto a floor or other hard surface in a manner that could damage or otherwise hinder the drive system of the pump device.

SUMMARY

Some embodiments of an infusion pump system may be configured to detect when at least one component of the pump system is exposed to an impact above a threshold level. In particular embodiments, the infusion pump system can be equipped with an impact detection system (also referred to herein as a "drop detector"). In such circumstances, the drop detector can sense when an impact above the threshold level has occurred to the pump device, which thereby enables the infusion pump system to initiate appropriate patient safety countermeasures. Appropriate patient safety counter measures can include, for example, disablement of medicine delivery by the pump device, emitting an alarm to the user, and prompting the user to perform a number of remedial actions. In embodiments in which the pump device is a single-use disposable component and the pump controller is a reusable component, the drop detector mechanism can be located in the pump device. Such a configuration can be useful because a significant impact imparted to the pump device component prior to connection (e.g., via a wired or wireless connection) with the controller component can be detected by the pump device component and identified by the controller component when the pump device component and controller component are initially connected. In such circumstances, the infusion pump system can initiate appropriate patient safety countermeasures prior to the patient's use of the system. If no such prior impact occurred, the system can be used in the normal fashion, and the drop detector system can continue to monitor for impacts above the threshold level while the pump device component and controller component are connected together. If such an impact is detected by the drop detector system while the pump device component and controller component are connected together, the infusion pump system can respond at that time by initiating appropriate patient safety countermeasures.

In particular embodiments, a portable infusion pump system may include a pump device including a pump housing that defines a space to receive a medicine. The pump device may optionally include a drive system positioned in the pump housing to dispense the medicine from the pump device when the medicine is received in the space of the pump housing. Further, the pump device may also include a drop detection mechanism mechanically mounted to a component of the pump housing. The drop detection mechanism can shift from a first configuration to a second configuration in response to an impact on the pump housing that is greater than or equal to a predetermined threshold level. Optionally, the portable infusion pump system may include a controller device removably attachable to the pump housing so as to electrically connect with the pump device. The controller device may house control circuitry configured to communicate with the drive system positioned in the pump housing to control dispensation of the medicine from the pump device.

Other embodiments include a medical infusion pump system. The medical infusion pump system may include a portable housing defining a space to receive a medicine and may optionally include a pump drive system to dispense medicine from the portable housing when the medicine is received in the space. The medical infusion pump system may include control circuitry that electrically communicates with the pump drive system to control dispensation of the medicine from the portable housing when the medicine is received in the space. Further, the medical infusion pump system may include a drop detector mechanism. The drop detector mechanism may optionally be mechanically mounted to the portable housing and in electrical communication with the control circuitry. The control circuitry can disable the pump drive system in response to the drop detector mechanism detecting an impact to the portable housing that is greater than or equal to a predetermined threshold level.

Some embodiments include a method of controlling a portable infusion pump system. The method may include sensing that a drop detector mechanism mounted to a portable infusion pump system indicates an impact greater than or equal to a predetermined threshold level was applied to the portable infusion pump system. The method may optionally include, in response to the sensing that the drop detector mechanism indicates said impact, disabling a pump drive system housed in the portable infusion pump system.

Some or all of the embodiments described herein may provide one or more of the following advantages. First, some embodiments of the infusion pump system may be configured to detect when the pump system has sustained an impact that could potentially damage the system or otherwise cause over-dosage or under-dosage of medicine to the user. Second, some embodiments of the infusion pump system may initiate user safety countermeasures upon detection that the system has sustained an impact above a threshold level. Third, certain embodiments of an infusion pump system may prevent use of a damaged system that may have some potential for delivery of an improper medicine dosage if used. Fourth, some embodiments of the infusion pump system may include a drop detector located in the single use pump device thereby providing passive user safety protection. Fifth, the infusion pump system may be configured to be portable, wearable, and (in some circumstances) concealable. For example, a user can conveniently wear the infusion pump system on the user's skin under clothing or can carry the pump system in the user's pocket (or other portable location) while receiving the medicine dispensed from the pump device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4-5 are perspective views of the pump device of FIGS. 1-2 being discarded and the controller device of FIGS. 1-2 being reused with a new pump device.

FIGS. 13A-13B are perspective views of an alternative embodiment of a drop detector mechanism, which can be implemented in the infusion pump system of FIG. 1 or another infusion pump system.

FIGS. 14-15 are perspective views of another alternative embodiment of a drop detector mechanism, which can be implemented in the infusion pump system of FIG. 1 or another infusion pump system.

DETAILED DESCRIPTION OF ILLUSTRATIVE EMBODIMENTS

Figure 1:
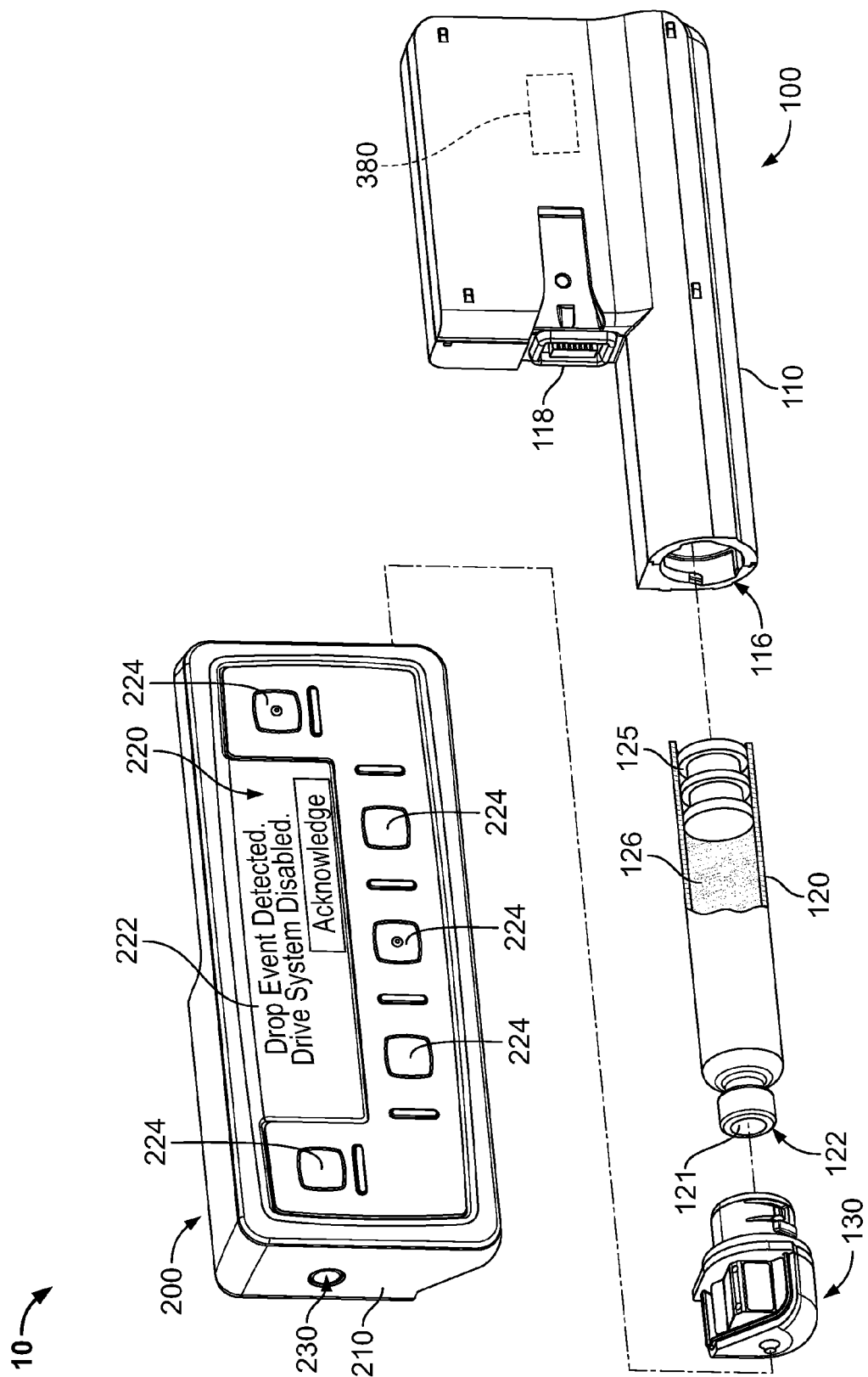
FIG. 1 is an exploded perspective view of an infusion pump system in accordance with some embodiments.

Referring to FIG. 1, an infusion pump system 10 can include a pump device 100 and a controller device 200 that communicates with the pump device 100. The pump device 100 in this embodiment includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system that advances a plunger 125 in the fluid cartridge 120 so as to dispense fluid therefrom.

As described in more detail below in connection with FIGS. 7-12, some embodiments of the pump device 100 can include an internal drop detector mechanism 380. The drop detector mechanism 380 can be configured to sense if the pump device 100 has received an impact force that is above a threshold level. The threshold level can be established below the level at which an impact may cause the pump device 100 to potentially malfunction or otherwise cause over-dosage or under-dosage of medicine to the user. In other words, an impact that may cause damage to the pump device 100 can be above the threshold level, and a drop detector system can be used to detect the impact. Such an impact may occur, for example, by dropping the pump device 100 onto a floor or other hard surface. When the pump device 100 and the controller device 200 are coupled (refer, for example, to FIG. 2), the drop detector mechanism 380 can be in electrical communication with a circuit housed in the controller device 200. In such a case, if the drop detector mechanism 380 previously detected an impact above the threshold level, the infusion pump system 10 can be configured to initiate appropriate user safety countermeasures. If no such impact was detected, the pump system 10 can proceed with normal operations. During normal operations, if the drop detector mechanism 380 then detects an impact force above the threshold level, the pump system 10 can respond by initiating appropriate user safety countermeasures. It should be understood from the description herein, that the term "drop detector" is not limited merely to detecting events in which the pump device is "dropped" onto a floor or other surface, but instead may also be suitable for detecting other impact events beyond mere drop events (e.g., impacts against walls or ceilings, impacts from external objects acting upon the pump device, and the like).

In some embodiments, the controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing, in a pouch clipped at the waist (e.g., similar to a cell phone pouch), or in the user's pocket while receiving the fluid dispensed from the pump device 100. Optionally, the controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 4-5, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics, as well as a rechargeable battery) while disposing of the relatively low-cost pump device 100 after each use. Such a pump system 10 can provide enhanced user safety as a new pump device 100' (and drive system therein) is employed with each new fluid cartridge 120'.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 can include a housing 210 having a number of features that mate with complementary features of the pump housing 110. In such circumstances, the controller device 200 can removably attach with the pump device 100 in a generally side-by-side configuration. The compact size permits the infusion pump system 10 to be discrete and portable (as described below in connection with FIG. 3). Moreover, at least one of the pump device 100 or the controller device 200 can include a release member that facilitates an easy-to-use detachment and replacement process.

Referring again to FIG. 1, the pump system 10 can be a medical infusion pump system that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, the pump housing structure 110 can include one or more retainer wings (not shown in FIG. 1) that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. In another example, the cap device 130 can be configured to irreversible attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the medicine cartridge 120 is emptied, expired, or otherwise exhausted).

Still referring to FIG. 1, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIG. 1) of the pump device 100. As described in more detail below, the pump device 100 can include a drive system that causes controlled dispensation of the medicine or other fluid from the cartridge 120. In some embodiments, the drive system incrementally advances a piston rod (not shown in FIG. 1) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device to the housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120. Power signals, such as signals from the rechargeable battery 245 (refer to FIG. 6) of the controller device 200 and from the power source 310 (refer to FIG. 7) of the pump device 100 may also be passed between the controller device 200 and the pump device 100.

As shown in FIG. 1, the pump device 100 can include an electrical connector 118 (e.g., having conductive pads, pins, and the like) that is exposed to the controller device 200 and that mates with a complementary electrical connector (refer to connector 218 in FIG. 2) on the adjacent face of the controller device 200. The electrical connectors 118 and 218 provide the electrical communication between the control circuitry (refer, for example, to FIG. 6) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. The electrical connectors 118 and 218 may similarly facilitate transmission of one or more power signals from the rechargeable battery pack 245 to the pump device 100, where the signals may be used to provide power to components of the pump device 100, or to transmit one or more power signals from the power source 310 to the controller device, where the signals may be used to charge the rechargeable battery 245 or to power components of the controller device 200.

Still referring to FIG. 1, the controller device 200 can include a user interface 220 that permits a user to monitor the operation of the pump device 100. In some embodiments, the user interface 220 can include a display device 222 and one or more user-selectable buttons (e.g., several buttons 224 are shown in the embodiment of FIG. 1). The display device 222 can include an active area in which numerals, text, symbols, images, or a combination thereof can be displayed. For example, the display device 222 can be used to communicate a number of settings or menu options for the infusion pump system 10. In this embodiment, the user may press one or more of the buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons of the user interface 220. For example, in embodiments of the infusion pump system 10 configured to dispense insulin, the user may press one or more of the buttons to change the dispensation rate of insulin or to request that a bolus of insulin be dispensed immediately or at a scheduled, later time. In some implementations, the display device 222 may also be used to communicate information regarding remaining battery life.

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

The controller device 200 can also be equipped with an inspection light device 230. The inspection light device 230 can provide the user with a tool to illuminate and inspect a targeted location. For example, the inspection light device 230 can be directed at the infusion site on the user's skin to verify that the infusion set is properly embedded, or the inspection light device 230 can be directed at the pump device 100 to illuminate the cavity 116 or other areas.

The inspection light device 230 can also be used to notify the user to an alert condition of the pump system 10. For example, as described further in reference to FIG. 12 below, the inspection light device 230 can be activated when the drop detector system has detected an impact greater than or equal to the threshold level. An activation of the inspection light device 230 can thereby provide a visual notification (as an alternative to, or in addition to, the visual notification provided on the display device 222) to the user that attention to the pump system 10 is warranted.

Figure 2:
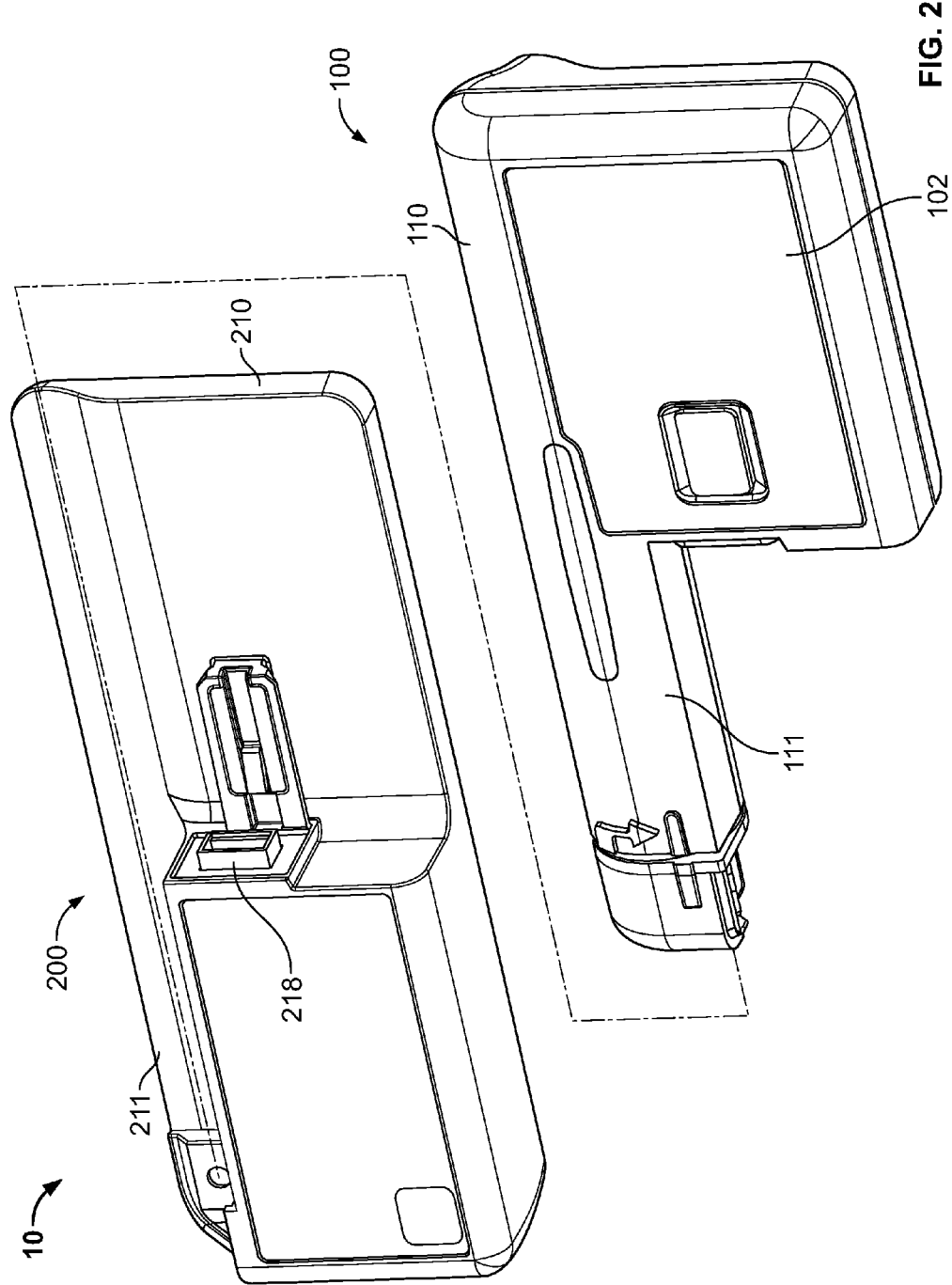
FIG. 2 is a perspective view of the infusion pump system of FIG. 1 in a detached state.

Referring now to FIG. 2, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 4) toward the controller device 200 until the complementary features connect and secure the separate components in the side-by-side arrangement. The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. In various implementations, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller device 200. Thus, the sensitive internal components in the controller device 200 and the pump device 100 can be reliably protected from water migration if the user encounters water (e.g., rain, incidental splashing, and the like) while using the pump system 10.

Figure 3:
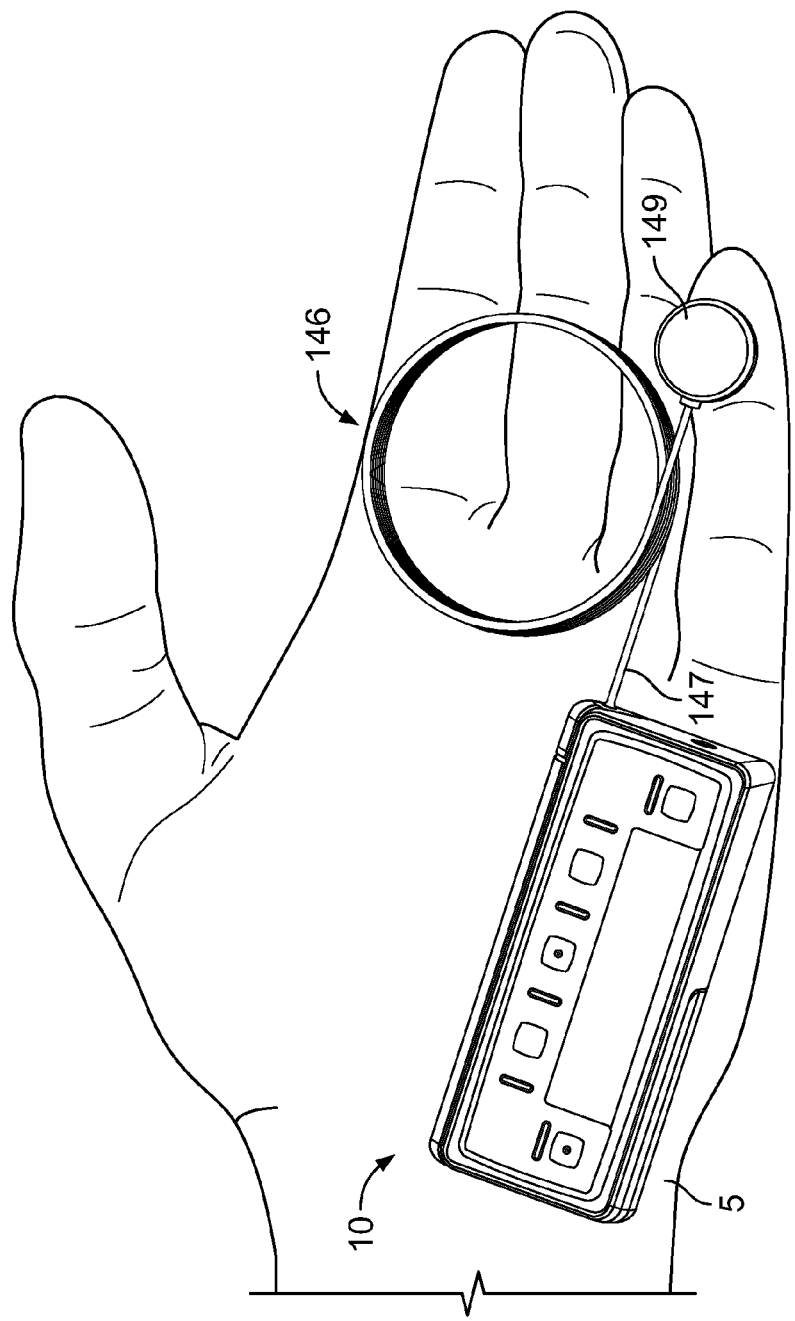
FIG. 3 is a perspective view of an infusion pump system, in accordance with some embodiments.

Referring to FIG. 3, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The pump system 10 is shown in FIG. 3 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

In some embodiments, the infusion pump system 10 can be pocket-sized so that the pump device 100 and controller device 200 can be worn in the user's pocket or in another portion of the user's clothing. In some circumstances, the user may desire to wear the pump system 10 in a more discrete manner. Accordingly, the user can pass the tube 147 from the pocket, under the user's clothing, and to the infusion site where the adhesive patch can be positioned. As such, the pump system 10 can be used to deliver medicine to the tissues or vasculature of the user in a portable, concealable, and discrete manner.

In some embodiments, the infusion pump system 10 can be configured to adhere to the user's skin directly at the location in which the skin is penetrated for medicine infusion. For example, a rear surface 102 (FIG. 2) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Referring now to FIGS. 4-5, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days—depending on the volume of medicine in the cartridge 120, the dispensation patterns that are selected for the individual user, and other factors. For example, a medicine cartridge 120 containing insulin can have an expected usage life of about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be collectively discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, the rechargeable battery pack 245, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics, and a rechargeable battery pack) while disposing of the relatively low-cost pump device 100 after each use. Such a pump system 10 can provide enhanced user safety as a new pump device 100' (and drive system therein) is employed with each new medicine cartridge 120'.

Referring to FIGS. 4-5, the same controller device 200 can be reused with a new pump device 100' having a new medicine cartridge 120' retained therein, and the previously used pump device 100, including the exhausted medicine cartridge, can be discarded in a discard bin 20. The new pump device 100' (FIG. 4) can have a similar appearance, form factor, and operation as the previously used pump device 100, and thus the new pump device 100' can be readily attached to the controller device 200 for controlled dispensation of medicine from the new medicine cartridge 120'. In some embodiments, the user can prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 4, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the cannula's adhesive patch to the user's skin. As shown in FIG. 4, the new medicine cartridge 120' may be filled with medicine such that the plunger 125 is not viewable through the barrel 111.

The new pump device 100' can be removably attached to the controller device 200 to assemble into the infusion pump system 10 for delivery of medicine to the user. As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction 219) that causes both a physical connection and an electrical connection. Thus, the infusion pump system 10 can permit users to readily join the pump device 100' and the controller device 200 without compound or otherwise difficult hand movements—a feature that can be particularly beneficial to child users or to elderly users.

Figure 6:
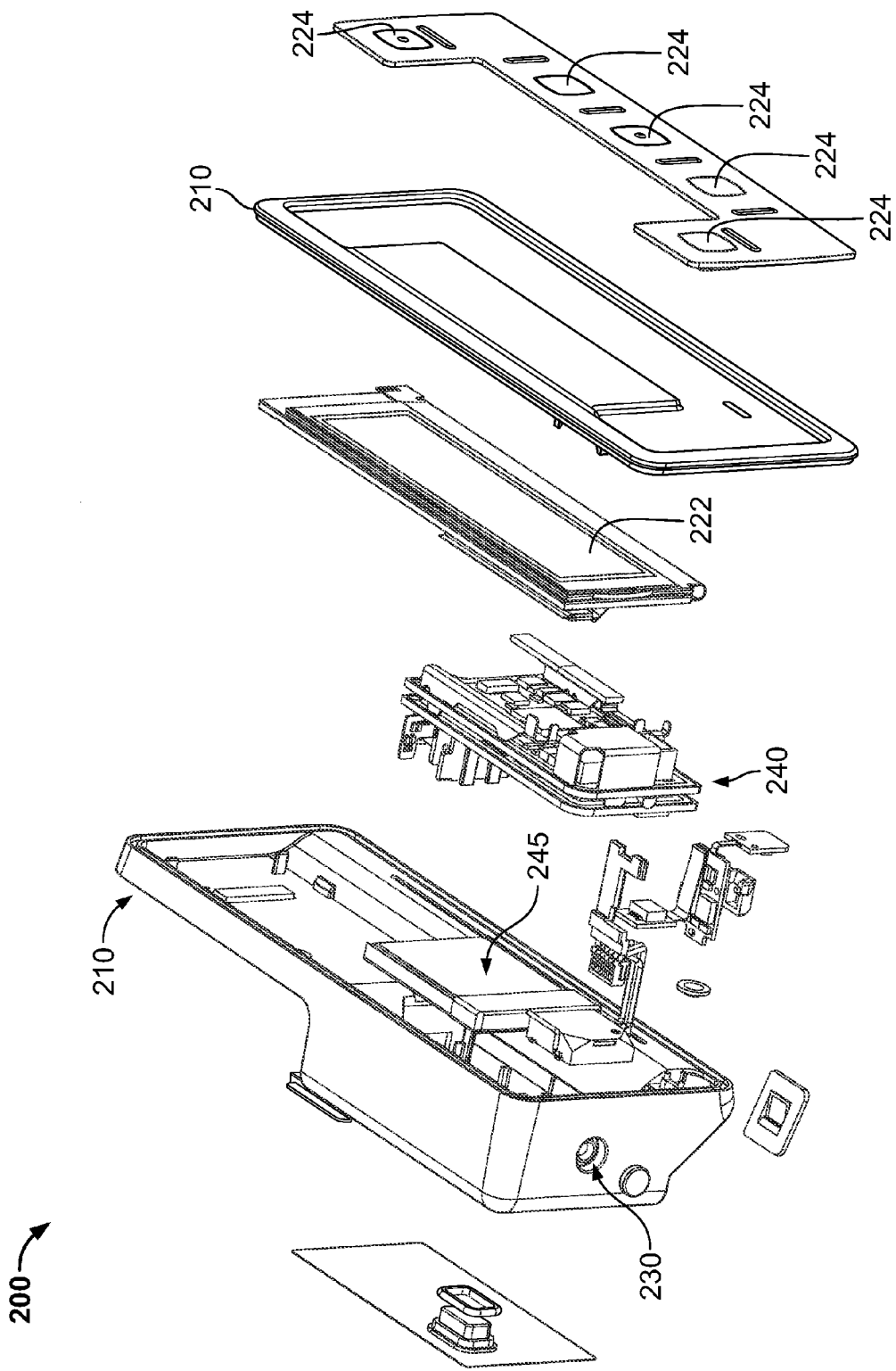
FIG. 6 is an exploded perspective view of a controller device for an infusion pump system, in accordance with some embodiments.

Referring now to FIG. 6, the controller device 200 (shown in an exploded view) houses a number of components that can be reused with a series of successive pump devices 100. In particular, the controller device 200 can include controller circuitry 240 and a rechargeable battery pack 245, each arranged in the controller housing 210. As described above, rechargeable battery pack 245 may provide electrical energy to components of controller circuitry 240, other components of the controller device (e.g., a display device 222 and other user interface components, sensors, or the like), or to components of the pump device 100. Controller circuitry 240 may be configured to communicate control or power signals to the drive system of the pump device 100, or to receive power or feedback signals from the pump device 100.

Still referring to FIG. 6, the user interface 220 of the controller device 200 can include input components and/or output components that are electrically connected to the controller circuitry 240. For example, the user interface 220 can include the display device 222 having an active area that outputs information to a user and buttons 224 that the user can use to provide input. Here, the display device 222 can be used to communicate a number of settings or menu options for the infusion pump system 10. In some embodiments, the controller circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The controller circuitry 240 can be programmable to cause the controller circuitry 240 to change any one of a number of settings for the infusion pump system 10. For example, the user may provide one or more instructions to adjust a number of settings for the operation of the infusion pump system 10. Such settings may be stored in one or more memory devices arranged in the controller circuitry 240.

As shown in FIG. 6, the infusion pump system 10 can be equipped with the inspection light device 230 to conveniently aid in visual inspection processes. For example, visual inspection and possible change of the infusion set 146 may be required in less than optimal conditions, including low-light conditions. Likewise, visual inspection of the pump housing cavity 116 (and the medicine cartridge 120 therein) may be required in low-light conditions. The user interface 220 of the controller device 200 can include an illuminated display screen 222 to facilitate the user's view of the display screen 222, but the inspection light device 230 provides a dedicated light source for illuminating targeted sites external to the controller device 200, for providing an alert notification, or a combination thereof.

The inspection light device 230 can include one or more user triggered light sources that are positioned to direct illumination at targeted objects outside of the pump system 10 or at components of the pump device 100. In the embodiment depicted in FIG. 6, the light source is arranged on the controller device 200. Such an arrangement provides close proximity to the control circuitry 240 housed in the controller device 200, thereby permitting the light source of the inspection light device 230 to be electrically connected to the control circuitry. In other embodiments, could be arranged on the pump device 100 or on both the controller device 200 and the pump device 100.

The inspection light device 230 can also be used to provide a visual notification to the user in the event of an alert or alarm condition. For example, as described further in reference to FIG. 12, the inspection light device 230 can be activated in response to detection by the drop detector system of an impact force to the pump system 10 above a threshold value at which a potential malfunction of the pump system 10 may be caused.

In some optional embodiments, the controller circuitry 240 can include a cable connector (e.g., a USB connection port or another data cable port) that is accessible on an external portion of the controller housing 210. As such, a cable can be connected to the controller circuitry 240 to upload data or program settings to the controller circuitry or to download data from the controller circuitry. For example, historical data of medicine delivery can be downloaded from the controller circuitry 240 (via the cable connector) to a computer system of a physician or a user for purposes of analysis and program adjustments. Optionally, the data cable can also provide recharging power.

Figure 7:
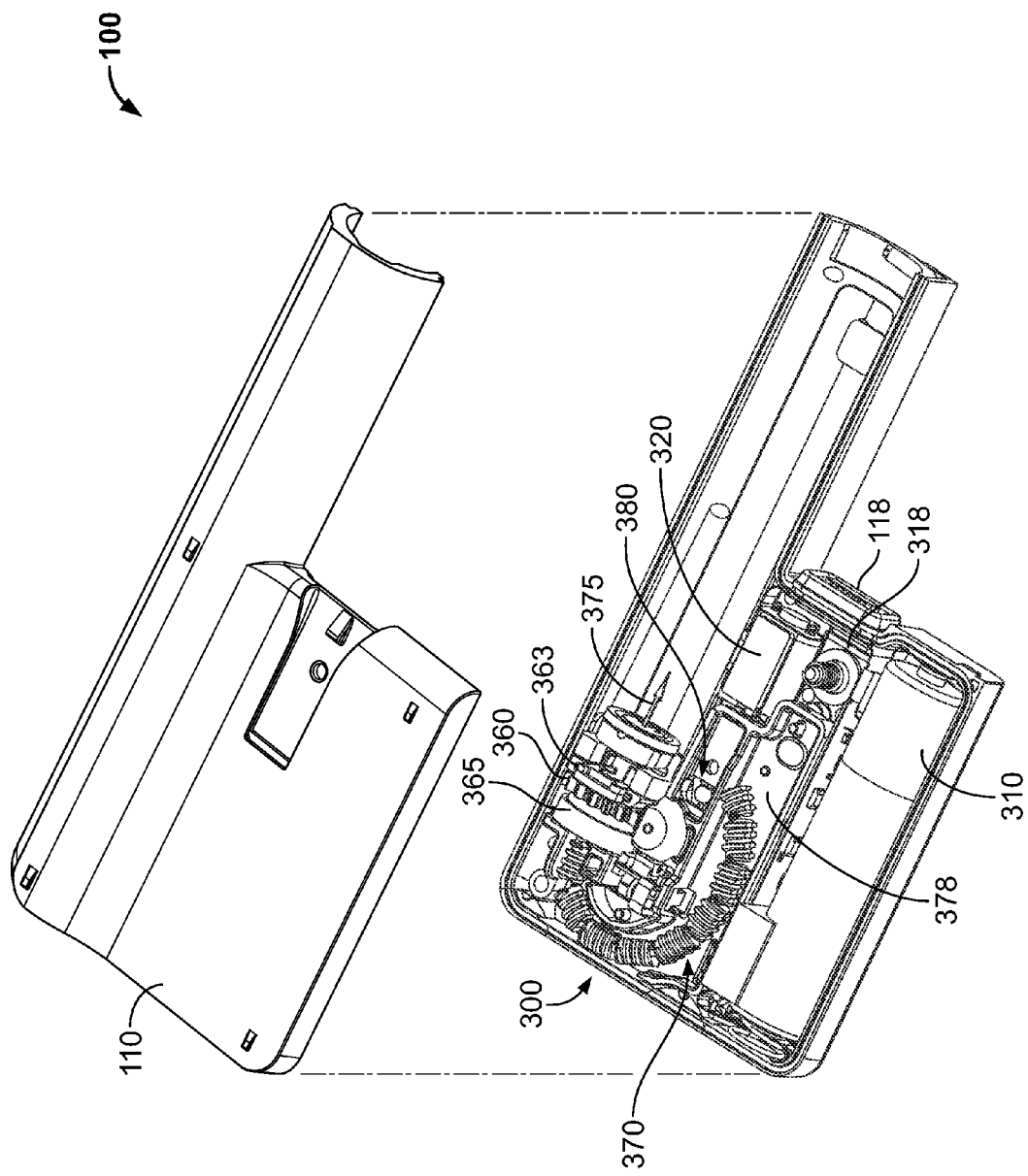
FIG. 7 is an exploded perspective view of a pump device for an infusion pump system, in accordance with some embodiments.

Referring now to FIG. 7, the pump device 100 can include a drive system 300 that is controlled by the controller device 200. As described in more detail below, the drive system 300 can incrementally dispense fluid in a controlled manner from cartridge 120 inserted into the pump device 100. Also, the pump device 100 may include a connector circuit 318 to facilitate the transfer of signals to and from the electrical connector 118. In some implementations, the connector circuit 318 in the pump device 100 may include a memory device that can store data regarding the pump device 100 and its operational history. As previously described, the electrical connector 118 of the pump device 100 can mate with the connector 218 (FIG. 2) of the controller device 200 so that electrical communication can occur between the pump device 100 and the controller device 200. In some embodiments, the connector circuit 318 can operate as a passageway to transmit electrical control signals from the controller circuitry 240 of the controller device 200 to the drive system 300. The connector circuit 318 can also operate as a passageway for the electrical power from a power source 310 housed in the pump device 100 to pass to the controller device 200 for recharging of the rechargeable battery 245. Furthermore, the connector circuit 318 can operate as a passageway for feedback signals from the drive system 300 to the controller circuitry 240 of the controller device 200.

In this embodiment, the pump device 100 houses the drive system 300 and the power source 310. For example, the power source 310 may comprise an alkaline battery cell, such as a 1.5 Volt "AAA" alkaline battery cell, which is contained in a dedicated space of the pump housing structure 110. The power source 310 may be capable of transmitting electrical energy to the controller device 200 when the pump device 100 is attached to the controller device 200, via connectors 118 and 218 as described above. For example, the power source 310 may be used to charge the rechargeable battery pack 245 when the pump device 100 is attached to the controller device 200. In some embodiments, the power source 310 is used to provide energy to the drive system 300 of the pump device 100, and also to electronic components of the controller device 200. In particular embodiments, the power source 310 may provide the energy to power all aspects of the infusion pump system 10. In some alternative embodiments, the rechargeable battery 245 housed in the controller 200 may provide the energy to power all aspects of the infusion pump system 10. In other embodiments, the rechargeable battery 245 and the power source 310 may each be responsible for powering particular aspects of the infusion pump system 10. In further embodiments, the rechargeable battery 245 may provide the energy to supplement the energy provided by the power source 310 to power aspects of the infusion pump system.

Still referring to FIG. 7, in some embodiment, the drive system 300 may include a number of components, such as an electrically powered actuator (e.g., reversible motor 320 or the like), a drive wheel 360, a bearing 365, a flexible piston rod 370, a piston rod guide 363, and a plunger engagement device 375. In this embodiment, the reversible motor 320 drives a gear system (not shown in FIG. 7) to cause the rotation of the drive wheel 360 that is coupled with the bearing 365. The drive wheel 360 may include a central aperture with an internal thread pattern, which mates with an external thread pattern on the flexible piston rod 370. The interface of the threaded portions of the drive wheel 360 and flexible piston rod 370 may be used to transmit force from the drive wheel to the piston rod 370. Accordingly, in the embodiment of FIG. 7, the drive wheel 360 is the driver while the flexible piston rod 370 is the driven member. As further described below, the rotation of the drive wheel 360 can drive the flexible piston rod 370 forward in a linear longitudinal direction.

Figure 8:
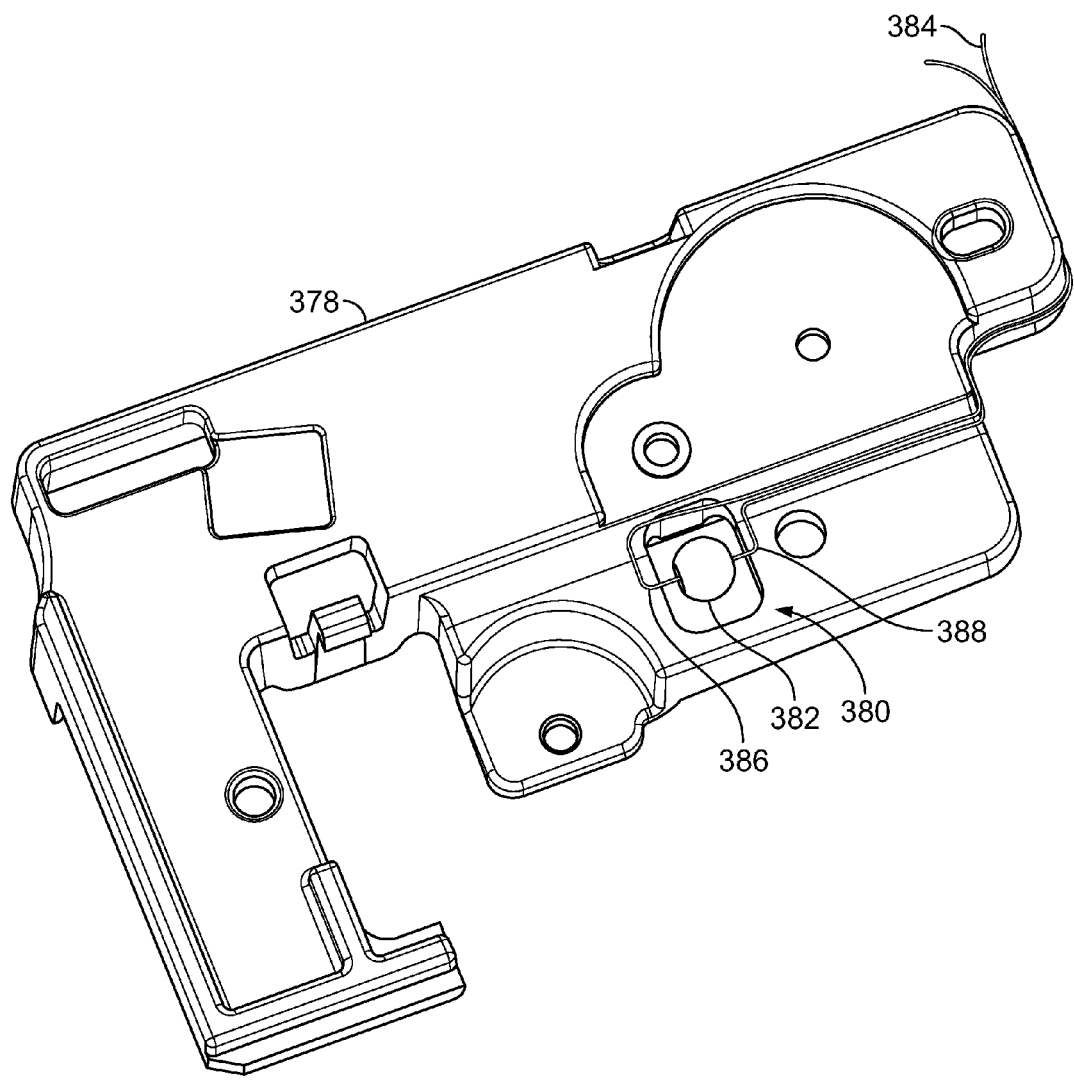
FIG. 8 is a perspective view of component portion of the pump device of FIG. 7, including a drop detector mechanism in accordance with some embodiments.

Referring now to FIGS. 7-8, the pump device 100 can also house the drop detector mechanism 380, which in this embodiment can be mounted on a component of the pump housing 110 such as an internal cover component 378. As previously described, the drop detector mechanism 380 can detect an impact to the pump device 100 that is greater than or equal to an impact threshold level. The impact threshold level can be established just below the range of impact that may induce the pump device 100 to potentially malfunction or otherwise cause over-dosage or under-dosage of medicine to the user. Consequently, the drop detector mechanism 380 can be capable of sensing impacts that are forceful enough to potentially induce damage to the pump device 100 or otherwise cause over-dosage or under-dosage of medicine to the user. In some embodiments, the drop detector mechanism 380 can be configured to detect an impact to the pump device 100 that is greater than or equal to a threshold level of about 1000 G to about 2000 G, and preferably about 1500 G. For example, in some embodiments, when an impact at or above the threshold level is detected by the drop detector mechanism 380, the drop detector mechanism 380, via a drop detection circuit 386 (FIG. 11), can communicate with the controller device 200 to initiate appropriate user safety countermeasures (some examples are described in connection with FIG. 12).

As shown in FIG. 8, the drop detector mechanism 380 can be mounted to the internal cover component 378 (as also depicted in FIG. 7) of the pump housing 110. For purposes of illustration in FIG. 8, the drop detector mechanism 380 and the internal cover component 378 are depicted while the other components of the pump device 100 are removed from view. In general, this example embodiment of the drop detector mechanism 380 includes a weighted bead 382 rigidly suspended on a conductive wire 384. In this embodiment, the drop detector mechanism 380 may employ the principle that an impact to the pump device 100 will create a momentum of the weighted bead 382 which will in turn induce stresses on the conductive wire 384. A higher level of impact will likewise result in higher stresses being induced in the conductive wire 384. At or above an impact force threshold level the conductive wire 384 will break as a result of the stresses induced by the weighted bead 382. The breakage of the conductive wire 384 can be electrically sensed and used to trigger appropriate user safety countermeasures for the pump system 10.

Accordingly, a number of factors can be used to affect the impact threshold level of the drop detector mechanism 380, such as the sizes and properties of the weighted bead 382 and the wire 384. The weighted bead 382 can comprise one or more of materials to provide the desired properties, such as the size and mass of the weighted bead 382. The mass of the weighted bead 382 can be selected so that an impact to the pump device 100 at or above the threshold level results in an appropriate momentum of the weighted bead 382 so as to break the conductive wire 384. In one embodiment, the weighted bead 382 can be made from copper and can have a mass of greater than approximately 5 mg, approximately 5 mg to approximately 25 mg, approximately 10 mg or approximately 20 mg, and approximately 15 mg to 16 mg in the depicted embodiment. Other materials such as stainless steel, brass, lead, and various metallic alloys can also be used to make the weighted bead 382. Preferably the weighted bead 382 can be made from non-corrosive material. The weighted bead 382 can be attached to the wire 384 by various means, such as gluing, crimping, soldering, clamping, or by an interference fit. In the example embodiment a UV curable adhesive can be used to join the weighted bead 382 to the wire 384. When the weighted bead 382 is installed into the pump device 100 a physical clearance space around the weighted bead 382 can allow the entire momentum from the weighted bead 392 to be transferred to the conductive wire 384.

The material properties and gauge of the conductive wire 384 can also be used to affect the impact threshold level of the drop detector mechanism 380. The ultimate tensile strength of conductive wire 384, for example, can determine how much stress from the weighted bead 382 (as a result of an impact force to the pump device 100) would be sufficient to break the conductive wire 384. The ultimate tensile strength of the conductive wire 384 can be affected by various factors such as, for example, the wire diameter or gauge. A wire with a larger diameter will have a higher ultimate tensile strength than a smaller diameter wire of the same material and construction. The type of material the wire is made from also affects the ultimate tensile strength. For example, a stainless steel wire can have a higher tensile strength than a copper wire of the same diameter, because stainless steel has a higher yield strength than copper. Further, wire can be constructed in various configurations such as solid, stranded, and braided. The type of construction can also affect the ultimate tensile strength of the wire. In the example embodiment depicted in FIG. 8, a 45 AWG solid copper wire is implemented in the drop detector mechanism 380. The material and size of the wire 384 can be selected to provide an ultimate tensile strength of approximately 20 grams to approximately 100 grams, and preferably 40 grams in the depicted embodiment. Various other combinations of materials, diameters, and construction configurations can also provide an appropriate ultimate tensile strength of conductive wire 384 in relation to a particular mass of the weighted bead 382.

Figure 11:
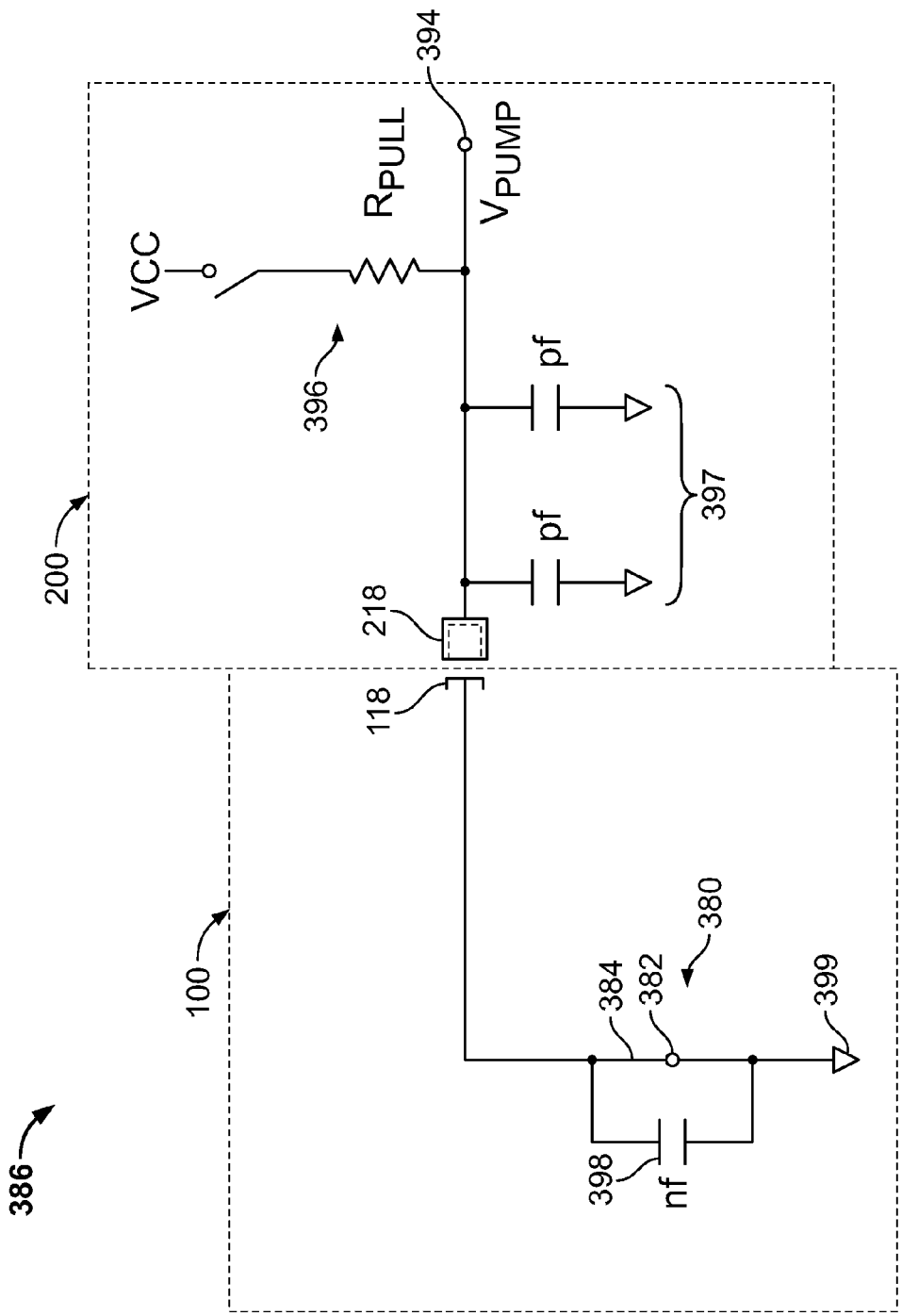
FIG. 11 is a schematic of drop detector circuit, in accordance with some embodiments.

Still referring to FIGS. 7-8, the conductive wire 384, in addition to being a mechanical element subject to tensile stress, may also serve as an electrical conductor used in the drop detection circuit 386 (refer to FIG. 11). In some embodiments, some or all of the outer surface of conductive wire 384 can be insulated to prevent it from shorting out from contact with other conductive elements within the pump device 100. In an example embodiment a nylon coating can be an insulating covering on conductive wire 384. Other types of insulating materials, such as enamel and PVC, can also be used. The ends of the conductive wire 384 can be electrically coupled with an electrical connector so as to become connected to an electrical circuit such as the drop detection circuit 386. In the example embodiment, the ends of conductive wire 384 can be connected to the electrical connector 118 of pump device 100 (FIG. 7.).

In general, the conductive wire 384 can be routed within the pump device 100 and secured to a framework in a manner that properly suspends the weighted bead 382 in a vacant space, thereby permitting the weighted bead 382 to move (and even break the wire 384) in the event of a significant impact to the pump device 100. As shown in FIG. 8, the conductive wire 384 can be mounted within pump device 100 to a framework such as the internal cover component 378 shown. The conductive wire 384 can be anchored to the framework at appropriate positions along the wire's path to properly secure it for protection. In addition, the conductive wire 384 can be anchored on each side of the weighted bead 384 so as to suspend the weighted bead 384 on the conductive wire 384 between two anchor points, such as anchor points 386 and 388. The conductive wire 384 can be anchored to the framework in various ways such as by clamping, crimping, soldering, tie-wrapping, and gluing. In an example embodiment, the conductive wire 384 is anchored to the internal cover component 378 using an adhesive. The adhesive can be applied in spots where particular mechanical attachment is beneficial, such as at anchor points 386 and 388, or applied continuously over the entire path of conductive wire 384.

Figure 9:
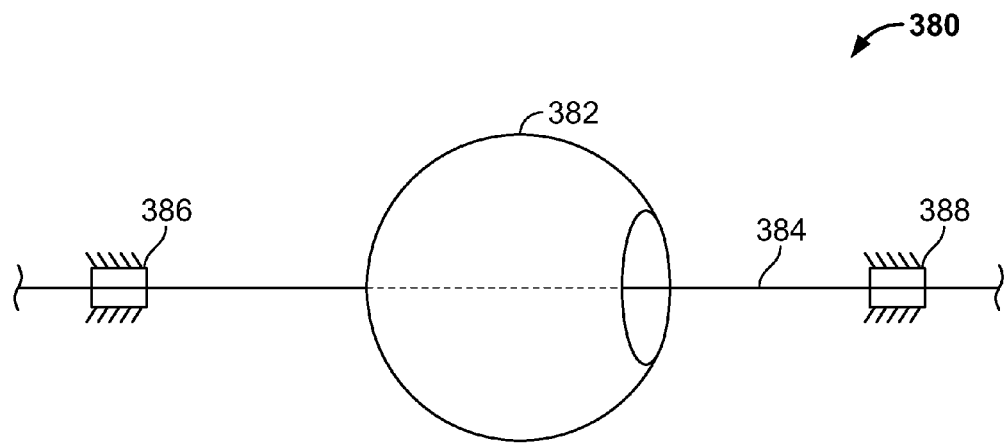
FIGS. 9-10 are schematic representations the drop detector mechanism of FIG. 8, in accordance with some embodiments.
Figure 10:
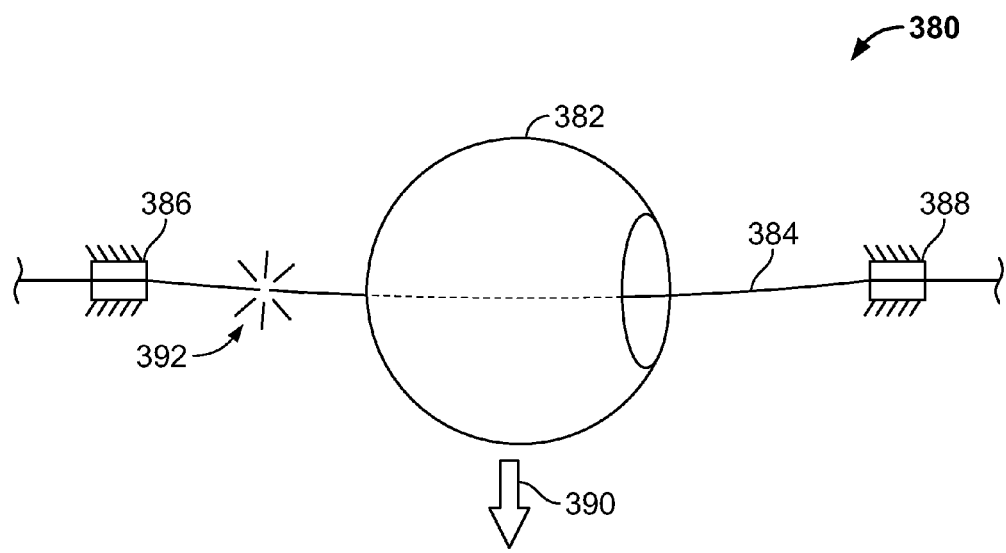

FIGS. 9 and 10 depict an example embodiment of a drop detector mechanism 380 in an enlarged view. In general, the example drop detector mechanism 380 can include the weighted bead 382 in suspension on the conductive wire 384. As previously described, the conductive wire 384 can be secured to a mounting framework at anchor points 386 and 388. When the drop detector mechanism 380 is subjected to an impact, such as from dropping pump device 100 onto a floor or a hard surface, a momentum force 390 can be created by weighted bead 382 (FIG. 10). The momentum force 390 can create a tensile stress in conductive wire 384 as a result of the physical orientation of the weighted bead 382 in suspension on the conductive wire 384 between the anchor points 386 and 388. When the impact is greater than or equal to a selected threshold level, the tensile stress imparted to the conductive wire 384 as a result of the momentum force 390 from the bead 382 is at or above the ultimate tensile strength of the conductive wire 384. In such a case, the conductive wire 384 can break, for example, at point 392. The breakage of the conductive wire 384 can be electrically sensed as a result of being an electrically conductive wire 384 in the drop detector circuit 386. When the drop detector circuit 386 has sensed a breakage of the conductive wire 384, the control circuitry in the controller device 200 can initiate appropriate user safety countermeasures for the pump system 10.

Referring now to FIG. 11, some embodiments of a drop detector circuit 386 can have a portion of its circuitry contained within the pump device 100, and a remaining portion of its circuitry contained within the controller device 200. The electrical connection between the portions of the drop detector circuit 386 can be made by the electrical connector 118 (FIG. 7) of pump device 100 being coupled to, and in electrical communication with, connector 218 (FIG. 2) of the controller device 200.

The controller device 200 can include a control circuitry that can monitor a voltage at input 394 of the drop detector circuit 386. The input 394 can be a digital input that is determined by the microprocessor to be either high (e.g., 5 volts) or low (e.g., approximately zero volts or ground). A voltage can be applied to the drop detector circuit by voltage source 396. The drop detection circuit 386 can include one or more capacitors 397 and 398, and a ground node 399. In an example embodiment, the capacitance value of the one or more capacitors 397 can be in the pico-Farad range, while the capacitance value of capacitor 398 can be in the nano-Farad range.

Still referring to FIG. 11, circuits with higher capacitance values take a longer time to charge (as represented by a circuit's RC time constant). Due to the substantial difference in capacitance values between the one or more capacitors 397 (pF range) and capacitors 398 (nF range), the RC time constant of the drop detection circuit 386 can be substantially affected by the various possible configurations of the drop detection circuit 386. In other words, the capacitance and RC time constant of the drop detection circuit 386 will vary depending on whether the pump device 100 is attached to the controller device 200, and whether the conductive wire 382 is intact so as to short-out the capacitor 398. As explained further below, the differences in time constants (i.e. how long it takes the circuit to charge) resulting from various configurations of the drop detection circuit 386 can be used by the control circuitry in the controller device 200 to determine the configuration or status of the drop detection circuit 386.

In general, the example drop detection circuit 386 can be in three different configurations: (1) a "normal" mode where pump device 100 and controller device 200 are coupled together, and the conductive wire 384 is intact; (2) a "disconnected" mode where the pump device 100 and the controller device 200 are not electrically connected; and (3) a "drop-detected" mode where the pump device 100 and the controller device 200 are coupled together, but the conductive wire 384 is broken (e.g., due to a significant impact on the pump device 100). One example implementation of the detection algorithm of the control circuitry in the controller device 200 for these three modes will now be explained in further detail.

In the aforementioned "normal" mode—where pump device 100 and controller device 200 are coupled together, and the conductive wire 384 is not broken—a voltage applied to the drop detector circuit 386 by voltage source 396 will be pulled to ground via ground node 399. As a result of the drop detection circuit 386 being grounded, the one or more capacitors 397 and 398 will not charge and the input 394 will remain low. The control circuitry of the controller device 200 can monitor the input 394 for a period of time after the application of a voltage by voltage source 396. If the input 394 remains low for a period of time that would otherwise have allowed for capacitors 398 and/or 397 to get charged if the drop detection circuit 386 was not grounded, then the control circuitry will determine that the pump system 10 is in the "normal" mode, and normal pump operations (e.g., dispensation of the medicine can proceed, along with other pump operations).

In the "disconnected" mode—where the controller device 200 is not coupled with the pump device 100 at connectors 118 and 218—a voltage applied to the drop detector circuit 386 by voltage source 396 will cause the one or more capacitors 397 to become charged. Because the capacitance value of the one or more capacitors 397 are relatively low (e.g., in the pico-Farad range compared to the capacitance value of capacitor 398 can be in the nano-Farad range), the drop detection circuit 386 will charge relatively quickly. The control circuitry in controller device 200 can detect the impedance from the input 394 to the ground (e.g., accounting for the one or more capacitors 397). Such an impedance value is measurably different from the "normal" mode where the input 394 is directly connected to the ground and from the "drop-detected" mode where the impedance is also affected by the capacitor 398 (described below). As such, the control circuitry in the controller device 200 can recognize the intermediate impedance value and readily determine that the pump system 10 is in the "disconnected" mode.

In the "drop-detected" mode—where the controller device 200 is coupled together with the pump device 100, but the conductive wire 384 is broken—a voltage applied to the drop detector circuit 386 by voltage source 396 will result in charging one or more capacitors 397 and the capacitor 398. The control circuitry in controller device 200 can detect the impedance from the input 394 to the ground (e.g., accounting for the one or more capacitors 397 and the capacitor 398, which has a relatively high capacitance value compared to one or more capacitors 397). Such an impedance value is measurably different from the "normal" mode where the input 394 is directly connected to the ground and from the "disconnected" mode where the impedance merely affected by the lower-capacitance-value of the one or more capacitors 397 (described above). As such, the control circuitry in the controller device 200 can recognize the substantially higher impedance value and readily determine that the pump system 10 is in the "drop-detected" mode. When the "drop-detected" mode is sensed, the controller device 200 can initiate appropriate user safety countermeasures for the pump system 10.

Figure 12:
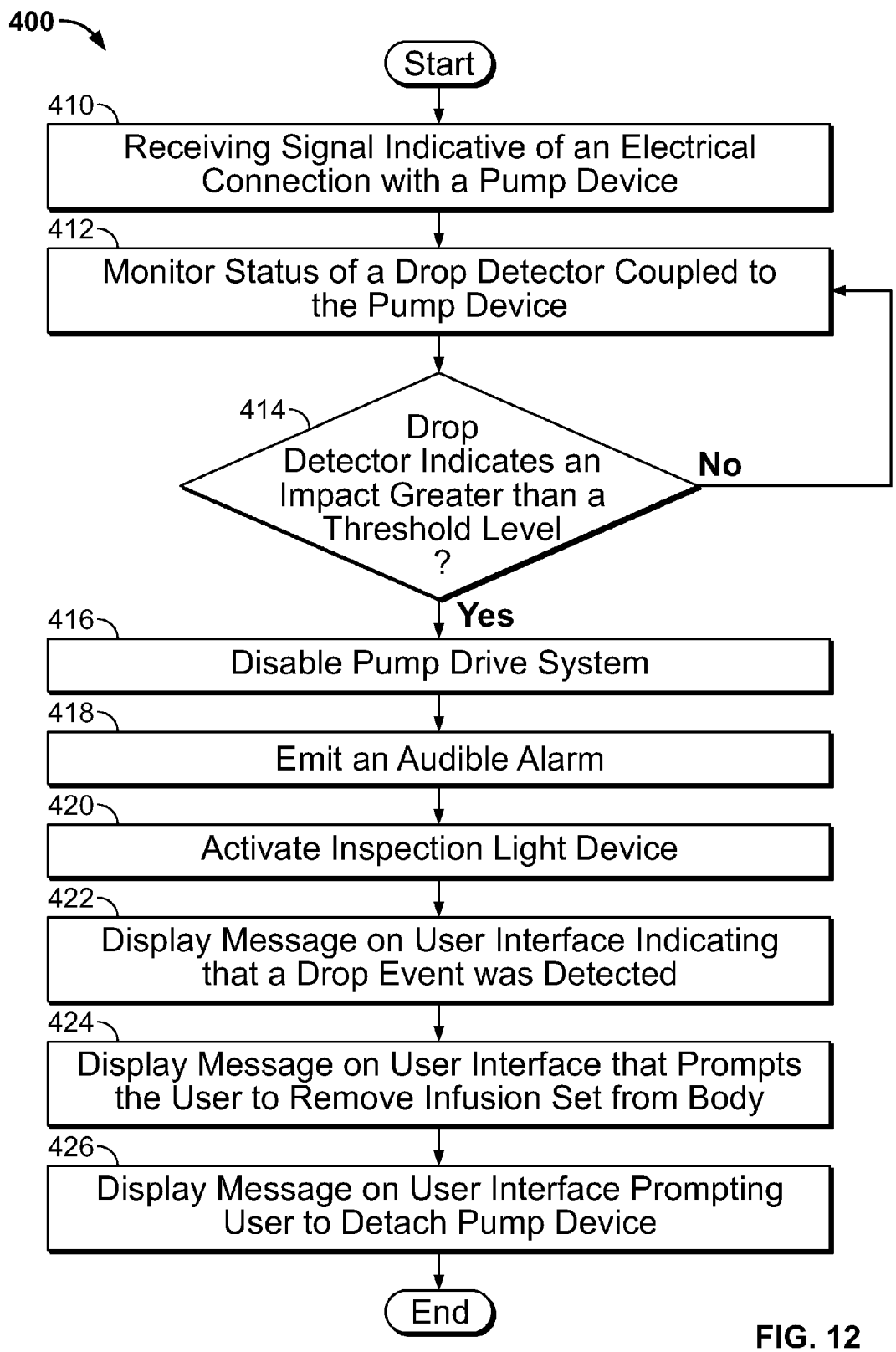
FIG. 12 is a flowchart describing a process of using a drop detector system of an infusion pump system in accordance with some embodiments.

Referring now to FIG. 12, a controller of an infusion pump system can implement a process 400 of detecting a drop event. Such a process 400, for example, can be implemented by the controller device 200 of the pump system 10 (FIG. 1). Alternatively, some operations of the process 400 could be implemented in an infusion pump device in which the controller and the pump drive system are integrated into a single housing.

In operation 410, the controller device can receive an electrical signal indicating that a pump device is electrically coupled with a controller device. For example, in the embodiments in which controller device 200 is separately housing from the pump device 100, the two components can be electrically connected via the connectors 118 and 218. As such, the signal can be a voltage at input 394 as described above in reference to FIG. 11. As previously described in connection with the drop detection circuit 386 (FIG. 11), when the electrical signal can be a signal indicative of one of the "normal" mode or the "drop-detected" mode.

In operation 412, the controller device monitors the status of the drop detection circuit. Such a monitoring operation can include periodic samplings of a drop detection circuit, such as the example drop detection circuit 386 (shown in FIG. 11). For example, if the drop detection circuit 386 indicates that the pump system 10 is in a "normal" mode, the monitoring operation 412 would reveal a signal that is different from the signal when in the "drop-detected" mode.

In operation 414, the controller device determines if the drop detector indicates an impact greater than or equal to a threshold level. For example, in the embodiment shown in FIGS. 8-11, the drop detector 380 can indicate that a significant impact occurred when the bead 382 caused the wire 384 to break, thereby causing the drop detection circuit 386 to provide a signal indicative of the "drop-detected" mode. If the drop detector does not indicate that an impact event occurred, the process 400 returns tot eh monitoring operation 412. If the "drop-detected" mode is signaled at a time after the pump device 100 is connected to the controller device 200 (e.g., the pump device 100 experienced a significant impact when attached to the controller device 200), the monitoring operation 412 would indicate that the drop detection circuit 386 to provided a signal indicative of the "drop-detected" mode rather than a previous signal indicative of the "mode" mode.

If the "drop-detected" mode is signaled immediately upon connect of the pump device 100 to the controller device 200 (e.g., the pump device 100 experienced a significant impact when separated from the controller device 200), the repeated cycle of monitoring the drop detection circuit could be bypassed.

Still referring to FIG. 12, if the drop detector indicates an impact greater than or equal to a threshold level, the controller device can respond according to some or all of the operations 416, 418, 420, 422, 424, and 426. In operation 416, in response to the controller device's determination that the drop detector system indicates the pump device 100 has sustained an impact at or above an impact threshold level (e.g., the "drop-detected" mode has been sensed), the controller device can act to disable the pump drive system. For purposes of safety, the pump system 10 may immediately stop the delivery of medicine to the user of the system. As described above, the cessation of medicine delivery can be an appropriate user safety precaution because an impact at or above the impact force threshold level can potentially damage the drive system 300 or the cartridge 120, whereby an over-dosage or under-dosage could occur. As an alternative to automatically disabling the pump drive system, the process 400 can instead include an operation in which the user is prompt to confirm/approve that the pump drive system can be disabled. In addition to (or in as an alternative to) disabling the pump drive system, the controller device can initiate further user safety countermeasures as described in the next steps of operation process 400.

In operation 418, the controller device can emit an audible alarm in response to a determination of an impact at or above the threshold level. The purpose of the audible alarm is to alert the user to the issue that the pump system 10 is not operating normally and requires attention. The audible alarm can be emitted before, after, or simultaneously with the operation 416 of disabling the drive system.

Optionally, in operation 420, a separate light device of the pump system can be activated to provide a visible alarm (in addition to the audible alarm of operation 418). For example, the inspection light device 230 of pump system 10 can be activated to provide a visual notification to the user to the issue that the pump system 10 is not operating normally and requires attention.

In operation 422, the controller device can display a message to indicate that a drop event was detected in response to a determination of an impact at or above the threshold level. For example, the user interface display screen 222 on the controller device 200 can display a short textual message to alert the user. The message can provide the user with an explanation of the reason for the audible and visual alarms. Further, the message can provide the user with an explanation that the pump drive system was automatically disabled.

In operation 424, the controller device can display a message prompting the user to remove the infusion set from the user's body. For example, the user interface display screen 222 on the controller device 200 can display the message prompting the user to remove the infusion set from the user's body. This message can be provided in order to assist the user with taking the proper actions to prevent an over dispensation of medicine tot eh user's body as a result of the detected impact.

Optionally, in operation 426, the controller device can display a message prompting the user to detach the pump device from the controller device. For example, the user interface display screen 222 on the controller device 200 can display a message prompting the user to detach the pump device 100 from the controller device 200. In order to resume use of the pump system 10, the pump device 100 that sustained an impact at or above the impact threshold level will need to be removed from the controller device 200 so that a new pump device, such as pump device 100' (refer to FIGS. 4 and 5) can be coupled with the controller device 200. This message assists the user to take the proper actions in response to the activation of the drop detection system, and to proceed towards resumption of the use of a properly functioning pump system 10.

Referring now to FIGS. 13A-B, some embodiments of the drop detector mechanism may be different from the single-wire embodiment depicted in FIG. 8. For example, an alternative embodiment of a drop detector mechanism 500 may include multiple different wires that are used to suspend at least one bead in a space defined by the pump housing, which can thereby provide a more accurate detection of impacts on the pump housing in any of a multiple different directions. This multi-wire embodiment of the drop detector mechanism 500 can be similar to the drop detector mechanism 380 of FIG. 8, but with the addition of a second conductive wire. In other words, this embodiment can have two conductive wires 512 and 514, rather than the single conductive wire 384 as in the embodiment shown in FIG. 8. The drop detector mechanism 500 can include a weighted bead 510 that is suspended on each of the two conductive wires 512 and 514. The two-wire drop detector mechanism 500 can be mounted onto a framework, such as the internal cover component 378 within the pump device 100 (similar to the embodiment described in connection with FIGS. 7-8). To cause the suspension of the two-wire weighted bead 510, the conductive wire 512 can be anchored to the framework at points 516 and 518, and the conductive wire 514 can be anchored to the framework at points 520 and 522.

In this embodiment, the drop detector 500 embodiment can provide a drop detector system that is not necessarily affected by the orientation of the pump device 100 in relation to the direction of an impact force. As FIG. 13B shows, conductive wires 512 and 514 can be arranged in a three-dimensional manner with respect to the weighted bead 510. Such an arrangement can increase the likelihood that, when the pump housing experiences an impact greater than or equal to a threshold level, the momentum from the weighted bead 510 will induce a breakage in at least one of the conductive wires 512 and 514, irrespective of the direction the impact force.

The drop detector 500 embodiment can be electrically connected in a drop detection circuit that is similar to the drop detection circuit 386 of FIG. 11. For example, the two conductive wires 512 and 514 can be electrically connected in series and wired into the drop detection circuit as is the single conductive wire 384 of the drop detection circuit 386. In this configuration, if either of the conductive wires 512 and 514 break, the microprocessor of the controller device 200 will determine the drop detection circuit is in a "drop-detected" mode—wherein the pump device 100 and the controller device 200 are coupled, but at least one of the conductive wires 512 or 514 is broken. In response, the controller device 200 can initiate appropriate user safety countermeasures for the pump system 10 (refer, for example, to FIG. 12).

Figure 15:
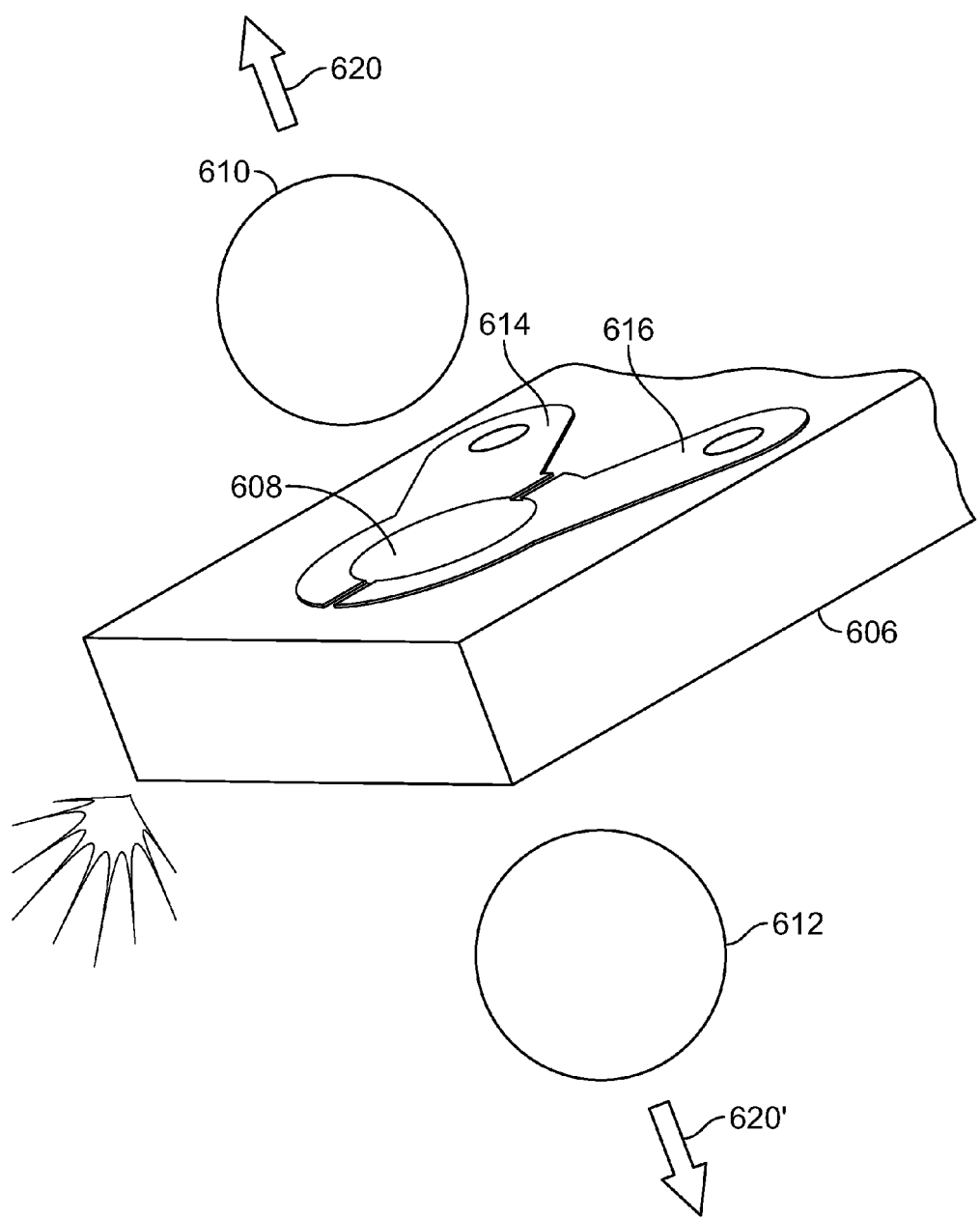

Referring now to FIGS. 14 and 15, other alternative embodiments of a drop detector mechanism may not include a wire to suspend a bead. For example, the drop detector mechanism 600 may include one or more magnetic elements that are moved in response to an impact on the pump housing greater than or equal to a threshold level. In the depicted embodiment, the components of the drop detector 600 can include two permanent magnetic balls 610 and 612, support member 606 with a through-hole 608, and electrical pads 614 and 616. The drop detector 600 components can be located within the pump device housing 110 of the pump device 100. For example, the support member 606 can be connected to or integrally formed with a pump housing component. The electrical pads 614 and 616 are formed on the surface of support member 606. The electrical pads 614 and 616 have a gap between them (as best seen in FIG. 15), so that they are not inherently in electrical communication. The magnetic balls 610 and 612 are electrically conductive. Magnetic balls 610 and 612 are seated in opposite sides of the opening in support member 606 created by through-hole 608. While seated in the through-hole 608, the magnetic balls 610 and 612 are not in direct physical contact with each other. The magnetic attraction force between the magnetic balls 610 and 612 can hold them in their seated position in through-hole 608. The magnetic attraction force can be strong enough to hold the magnetic balls 610 and 612 in their seated positions even while the pump device 100 is physically moved around during normal use.

During operation of the drop detector 600, the magnetic balls 610 and 612 can be seated in their respective positions at least partially along the through-hole 608 of support member 606. At least a first magnetic ball 610 can be in physical contact with both electrical pads 614 and 616. Because the first magnetic ball 610 is electrically conductive, the physical contact of magnetic ball 610 with electrical pads 614 and 616 can cause the electrical pads 614 and 616 to be in electrical communication with each other. The electrical pads 614 and 616 can be wired within a drop detection circuit similar to the drop detection circuit 386 (refer to FIG. 11), but wherein the electrical pads 614 and 616 are connected into the drop detection circuit to take the place of the conductive wire 384. In other words, the combination of electrical pads 614 and 616 and the magnetic ball 610 can create an electrical circuit that can be electrically wired to short out a capacitor like the conductive wire 384 does in the drop detection circuit 386 of FIG. 11. In this manner, when the magnetic balls 610 and 612 are in their seated positions, the microprocessor of controller device 200 can sense that the drop detection circuit is configured in its normal mode, and the pump system 10 can be allowed to function as normal.

The drop detector 600 can detect an impact to the pump device 100 at or above an impact threshold level in the following manner. As depicted in FIG. 15, an impact to the pump device 100 can create a separation force 620 and 620' for each of the magnetic balls 610 and 612. The physical characteristics of the magnetic balls 610 and 612 and the support member 606 with through-hole 608 can be designed so that an impact above the impact threshold level will create a separation force that is greater than the force of magnetic attraction between the magnetic balls 610 and 612 when they are configured as shown. In such a case, if separation force applied to the magnetic balls 610 and 612 as a result of an impact to pump device 100 is greater than or equal to the impact threshold level, the separation force 620 and 620' can overcome the force of magnetic attraction between the magnetic balls 610 and 612, and magnetic ball 610 will physically separate from the electrical pads 614 and 616. When the magnetic ball 610 physically separates from the electrical pads 614 and 616, the pads will no longer be in electrical communication with each other (e.g., the electrical circuit formed by the combination of electrical pads 614/616 and magnetic ball 610 can be broken). With the electrical pads 614 and 616 wired into a drop detection circuit similar to the drop detection circuit 386, and an open circuit between the electrical pads 614 and 616, the microprocessor of controller device 200 can sense that the drop detection circuit has entered the drop-detected mode.

The microprocessor of controller device 200 can then initiate appropriate user safety countermeasures for the pump system 10 (refer to FIG. 12). Preferably, the pump housing 110 can be configured to provide sufficient physical clearance for the displacement of magnetic balls 610 and 612 created by an impact at or above the impact threshold level. When the magnetic balls 610 and 612 separate from the support member 606 as the result of an impact to the pump device 100, the magnetic balls 610 and 612 will move away from the support member 606 far enough so that they do not automatically reseat themselves as a result of the force of magnetic attraction between them. As an alternative to relying on the distance of physical displacement between the dislodged magnetic balls 610 and 612, a physical barrier device, such as a one-way flap or a labyrinth structure can be used to ensure the magnetic balls 610 and 612 do not automatically reseat themselves onto through-hole 608.

Figure 16:
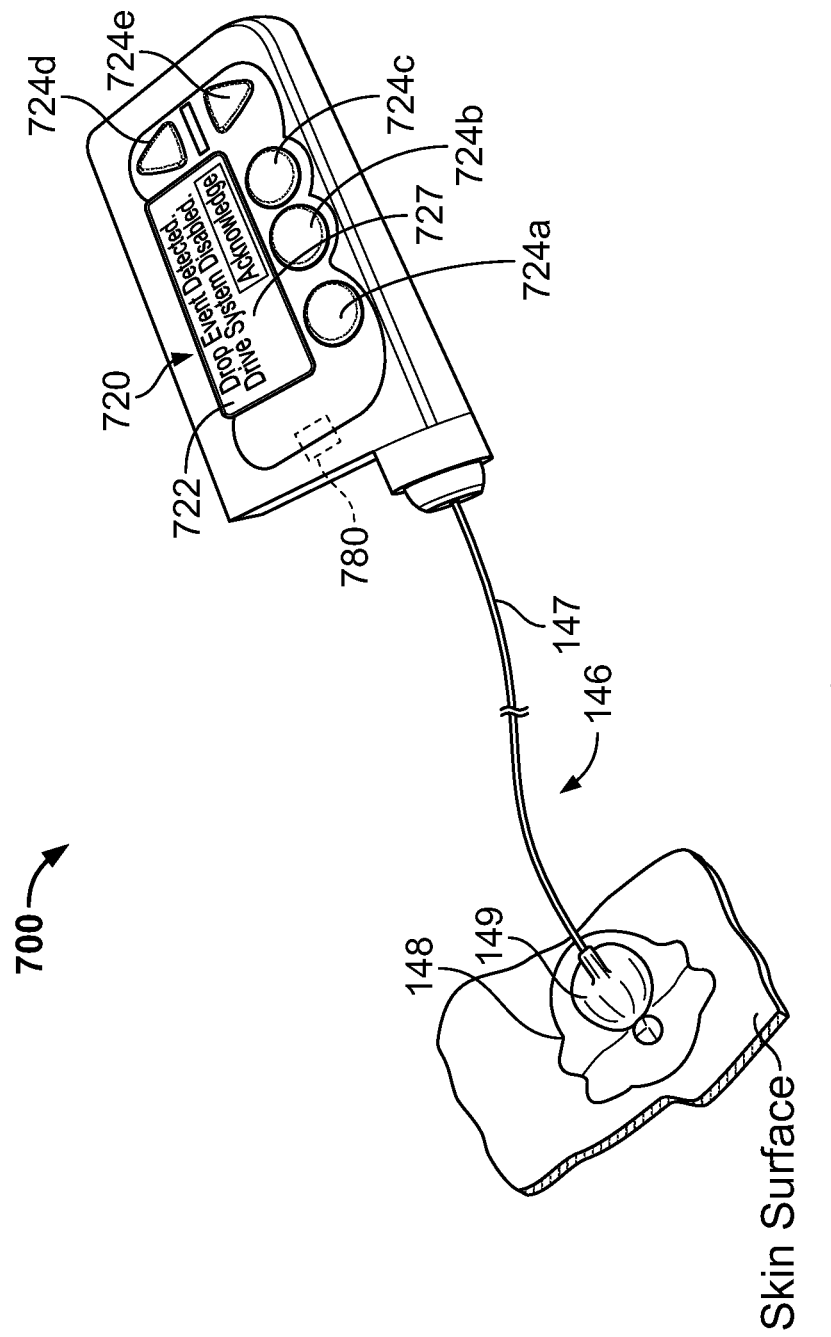
FIG. 16 is a perspective view of an alternative infusion pump system in accordance with some embodiments Like reference symbols in the various drawings indicate like elements.

Referring now to FIG. 16, some embodiments of a portable infusion pump system 700 having a drop detector mechanism 780 can employ a reusable pump apparatus (rather than a disposable pump device as previously described). In such circumstances, the infusion pump system 700 may comprise a reusable device that houses the control circuitry and the pump drive system within a single housing construct. In the particular embodiment depicted in FIG. 16, the pump system 700 comprises a reusable pump device that houses both the controller circuitry and the pump drive system. Similar to previously described embodiments, the pump system 700 can include a housing structure that defines a cavity in which a medicine cartridge can be received (not shown in FIG. 16; refer for example to cartridge 120 in FIG. 1). For example, the pump system 700 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. In this embodiment, the user can wear the portable pump system 700 on the user's skin under clothing or in the user's pocket while receiving the medicine dispensed through the infusion set 146.

Similar to previously described embodiments, the infusion pump system 700 may include the drop detector mechanism 780 that can detect an impact greater than or equal to an impact threshold level. The threshold level can be established below the level at which an impact may cause the infusion pump system 700 to potentially malfunction or otherwise cause over-dosage or under-dosage of medicine to the user. Such an impact may occur, for example, by dropping the infusion pump system 700 onto a floor or other hard surface, and by subjecting the infusion pump system 700 other types of impacts.

Accordingly, the drop detector mechanism 780 of the infusion pump system 700 can be constructed like any of the embodiments described above, such as the single-wire embodiment depicted in FIG. 8, the multi-wire embodiment depicted in FIGS. 13A-B, or the magnetic member embodiment depicted in FIG. 14. Alternatively, the drop detector mechanism 780 can include a sensor circuit device (e.g., in the form of an IC chip or the like) mounted to a control board. This type of sensor circuit may include one or more accelerometers configured to measure impacts that are impacted to the housing of the system 700, and then communicate with the control circuitry of the system 700 so that the infusion pump system 700 can initiate appropriate user safety countermeasures if the detected impact was greater than or equal to the predetermined threshold level.

In some embodiments, the drop detector circuitry for use with the mechanism 780 can be similar to the drop detection circuit 386 described in reference to FIG. 11, but with a few adaptations. For example, because the infusion pump system 700 has a single housing, the drop detector circuit may not necessarily communicate via the electrical connectors 118 and 218. Further, the one or more capacitors 397 (FIG. 11) may not be necessary because there is not a need to detect whether a separate pump device is connected to a controller device. Consequently, the drop detection circuit used with the drop detector mechanism 780 in the infusion pump system 700 may optionally be a simplified version of the drop detection circuit 386 depicted in FIG. 11.

Still referring to FIG. 16, the user interface 720 of the pump system 700 includes a display device 722 and one or more user-selectable buttons 724*a-e*. The display device 722 can include an active area in which numerals, text, symbols, images, or a combination thereof can be displayed (as shown, for example, in FIG. 16). For example, the display device 722 can be used to communicate to the user that a drop event has been detected and the drive system has been disabled (similar to the process described in reference to FIG. 12). Also, the display device 722 can be used to communicate a number of settings or menu options for the infusion pump system 700. For example, the display device 722 can be used to communicate medicinal delivery information 727, such as the basal delivery rate, a bolus dosage, a historical record of medicine delivered, the amount of medicine remaining in the cartridge, or the like. In another example, the display device 722 can be used to communicate time and date information, which can be used by the user to determine dosage schedules, bolus delivery times, meal times, or the like.

Accordingly, the user may press one or more of the buttons 724*a*, 724*b*, 724*c*, 724*d*, and 724*e* to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). Also, the user can adjust the settings or otherwise program the pump system 700 by pressing one or more buttons 724*a*, 724*b*, 724*c*, 724*d*, and 724*e* of the user interface 420. Thus, the user can contemporaneously monitor the operation of the pump system 700, including any messages pertaining to the drop detection system from the same user interface 720.

A number of embodiments of the invention have been described. Nevertheless, it will be understood that various modifications may be made without departing from the spirit and scope of the invention. Accordingly, other embodiments are within the scope of the following claims.

What is claimed is:

1. A portable infusion pump system, comprising:
a pump device including a pump housing that defines a space to receive a medicine, a drive system positioned in the pump housing to dispense the medicine from the pump device when the medicine is received in the space of the pump housing, and a drop detection mechanism mechanically mounted to a component of the pump housing, wherein the drop detection mechanism shifts from a first configuration to a second configuration in response to an impact on the pump housing that is greater than or equal to a predetermined threshold level; wherein the drop detection mechanism comprises a weighted member suspended in a spaced from one or more electrically conductive wires coupled to a circuit, wherein the drop detector mechanism shifts from the first configuration to the second configuration when at least one of the wires is broken; and
a controller device removably attachable to the pump housing so as to electrically connect with the pump device, wherein the controller device houses control circuitry configured to communicate with the drive system positioned in the pump housing to control dispensation of the medicine from the pump device.

2. The portable infusion pump system of claim 1, wherein the drop detection mechanism is connected to a first portion of a drop detection circuit housed in the pump housing, the first portion of a drop detection circuit being in electrical communication with a second portion of a drop detection circuit housed in the controller device.

3. The portable infusion pump system of claim 2, wherein the drop detection circuit is in electrical communication with the control circuitry housed in the controller device so that the control circuitry initiates an alarm when the drop detection circuit indicates the drop detection mechanism is in the second configuration.

4. The portable infusion pump system of claim 1, wherein, in response to the drop detection mechanism shifting from the first configuration to the second configured, the control circuitry is configured to disable the drive system, activate an audible alarm, and display of one or more messages on a user interface display located on the controller device.

5. The portable infusion pump system of claim 1, wherein the drop detection mechanism comprises one or more magnetic members engaged with a portion of a drop detection circuit, wherein the drop detector mechanism shifts from the first configuration to the second configuration when the one or more magnetic members are disengaged from the portion of the drop detection circuit.

6. The portable infusion pump system of claim 1, wherein the pump device is a one-time-use device equipped with one or more structures configured to prevent reuse of the pump device, wherein the pump housing includes an interior wall that defines a space to slidably receives an outer wall of a pre-filled medicine cartridge insertable through an opening defined by the pump housing, wherein the pump device further comprises a cap device that directly engages with the pump housing to enclose the pre-filled medicine cartridge in the pump housing when the pre-filled medicine cartridge is received in the space of the pump housing, and wherein the controller device is a reusable controller device including: a controller housing that is removably attachable to the pump housing in a fixed relationship; one or more electrical contacts disposed on the controller housing, the electrical contacts of the controller device being engageable with corresponding electrical contacts of the pump device when removably attached.

7. A medical infusion pump system, comprising:
a portable housing defining a space to receive a medicine;
a pump drive system to dispense medicine from the portable housing when the medicine is received in the space;
control circuitry that electrically communicates with the pump drive system to control dispensation of the medicine from the portable housing when the medicine is received in the space;
a drop detector mechanism mechanically mounted to the portable housing and in electrical communication with the control circuitry, wherein the control circuitry disables the pump drive system in response to the drop detector mechanism detecting an impact to the portable housing that is greater than or equal to a predetermined threshold level; and wherein the drop detection mechanism comprises a weighted member suspended in a spaced from one or more electrically conductive wires coupled to a circuit, wherein the drop detector mechanism shifts from the first configuration to the second configuration when at least one of the wires is broken.

8. The medical infusion pump system of claim 7, wherein the drop detector mechanism is configured to respond to the impact to the portable housing that is greater than or equal to the predetermined threshold level, and wherein the control circuitry is in electrical communication with the drop detector mechanism so that the control circuitry initiates an alarm when the drop detector mechanism indicates an exposure of the impact to the portable housing that is greater than or equal to the predetermined threshold level.

9. The medical infusion pump system of claim 8, wherein the drop detector mechanism comprises a weighted member suspended in an interior space from one or more electrically conductive wires coupled to a drop detection circuit, and wherein the drop detector mechanism is configured to respond to the impact that is greater than or equal to the predetermined threshold level by shifting from a first configuration in which the one or more wires are unbroken to a second configuration in which at least one of the wires is broken.

10. The medical infusion pump system of claim 8, wherein the drop detector mechanism comprises one or more magnetic members engaged with a portion of a drop detection circuit, and wherein the drop detector mechanism is configured to respond to the impact that is greater than or equal to the predetermined threshold level shifting the one or more magnetic members to a disengaged position relative to the drop detection circuit.

11. The medical infusion pump system of claim 7, wherein the drop detector mechanism comprises one or more accelerometers.

12. The medical infusion pump system of claim 7, wherein the control circuitry initiates an audible alarm in response to the drop detector mechanism detecting an impact to the portable housing that is greater than or equal to a predetermined threshold level.

13. The medical infusion pump system of claim 12, wherein, in response to the drop detector mechanism detecting an impact to the portable housing that is greater than or equal to a predetermined threshold level, the control circuitry causes a display of one or more alert messages on a user interface display located on the infusion pump system and causes an inspection light to illuminate, the inspection light being different from the user interface display.

14. The medical infusion pump system of claim 7, wherein the control circuitry is housed in a controller housing that is removably attachable to the portable housing.

15. The medical infusion pump system of claim 14, wherein the pump drive system is housed in the portable housing, and one or more electrical contacts disposed on the controller housing are engageable with corresponding electrical contacts disposed on the portable housing when the controller housing is removably attached to the portable housing.

16. A method of controlling a portable infusion pump system, comprising:
sensing that a drop detector mechanism mounted to a portable infusion pump system indicates an impact greater than or equal to a predetermined threshold level was applied to the portable infusion pump system; wherein the drop detection mechanism comprises a weighted member suspended in a spaced from one or more electrically conductive wires coupled to a circuit, wherein the drop detector mechanism shifts from the first configuration to the second configuration when at least one of the wires is broken; and
in response to the sensing that the drop detector mechanism indicates said impact, disabling a pump drive system housed in the portable infusion pump system.

17. The method of claim 16, further comprising in response to the sensing that the drop detector mechanism indicates said impact, emitting an audible alarm.

18. The method of claim 17, further comprising in response to the sensing that the drop detector mechanism indicates said impact, displaying one or more alert messages on a user interface display of the portable infusion pump system.

19. The method of claim 18, further comprising in response to the sensing that the drop detector mechanism indicates said impact, activating a light source of the portable infusion pump system that is different from the user interface display.

* * * * *